(12) United States Patent
Patke et al.

(10) Patent No.: US 6,183,511 B1
(45) Date of Patent: Feb. 6, 2001

(54) BILEAFLET HEART VALVE HAVING OPEN CHANNEL AND SWIVEL PIVOTS

(75) Inventors: Nandkishor G. Patke, Shoreview; Adel A. Mikhail, Bloomington; Gene E. Stobbs, Brooklyn Park, all of MN (US)

(73) Assignee: CV Dynamics, Inc., Inver Grove Heights, MN (US)

( * ) Notice: Under 35 U.S.C. 154(b), the term of this patent shall be extended for 0 days.

(21) Appl. No.: 09/165,442

(22) Filed: Oct. 2, 1998

Related U.S. Application Data

(60) Provisional application No. 60/060,922, filed on Oct. 3, 1997.

(51) Int. Cl.[7] ........................................................ A61F 2/24
(52) U.S. Cl. ............................................................. 623/2.28
(58) Field of Search ...................................... 623/2.1, 2.12, 623/2.17, 2.21, 2.22, 2.36, 2.38, 900, 2.28

(56) References Cited

U.S. PATENT DOCUMENTS

| | | | |
|---|---|---|---|
| 4,308,624 | * | 1/1982 | Klawitter .................................. 623/2 |
| 4,451,937 | * | 6/1984 | Klawitter .................................. 623/2 |
| 4,692,165 | * | 9/1987 | Bokros ...................................... 623/2 |
| 4,863,459 | * | 9/1989 | Olin .......................................... 623/2 |
| 4,908,028 | * | 3/1990 | Colon et al. .............................. 623/2 |
| 4,995,881 | * | 2/1991 | Knoch et al. ............................. 623/2 |
| 5,026,391 | * | 6/1991 | McQueen et al. ........................ 623/2 |
| 5,116,366 | * | 5/1992 | Hwang ...................................... 623/2 |
| 5,314,467 | * | 5/1994 | Shu ............................................ 623/2 |
| 5,326,372 | * | 7/1994 | Mhatre et al. ............................. 623/2 |

* cited by examiner

Primary Examiner—Michael J. Milano
(74) Attorney, Agent, or Firm—Moore & Hansen

(57) ABSTRACT

A bileaflet heart valve comprising an annular base and pivoting leaflets. Each leaflet is "free-floating" within recesses without fixed rotational axis in order to increase translational movement and redistribute stresses. Each recess fluidly communicates with a groove extending at least partially around the inner surface of the annular base and fluid flow is directed through the recesses at different angles during antegrade circulation, retrograde circulation, and valve closure. A recess entrance angle to each of the recesses preferably being less than about 35° and the pivoting mechanism within the recess including first and second fulcrum edges of each leaflet shiftably engaged with side surfaces of the respective recesses. The leaflets have a beveled bottom side having two separate planar surfaces which lie at an angle to one another. In preferred embodiments, an upper planar surface of the bottom surface of each leaflet lies at an angle of greater than ninety (90) degrees with respect to a horizontal passing through a section of the annular base when the leaflet is in a fully open position.

17 Claims, 13 Drawing Sheets

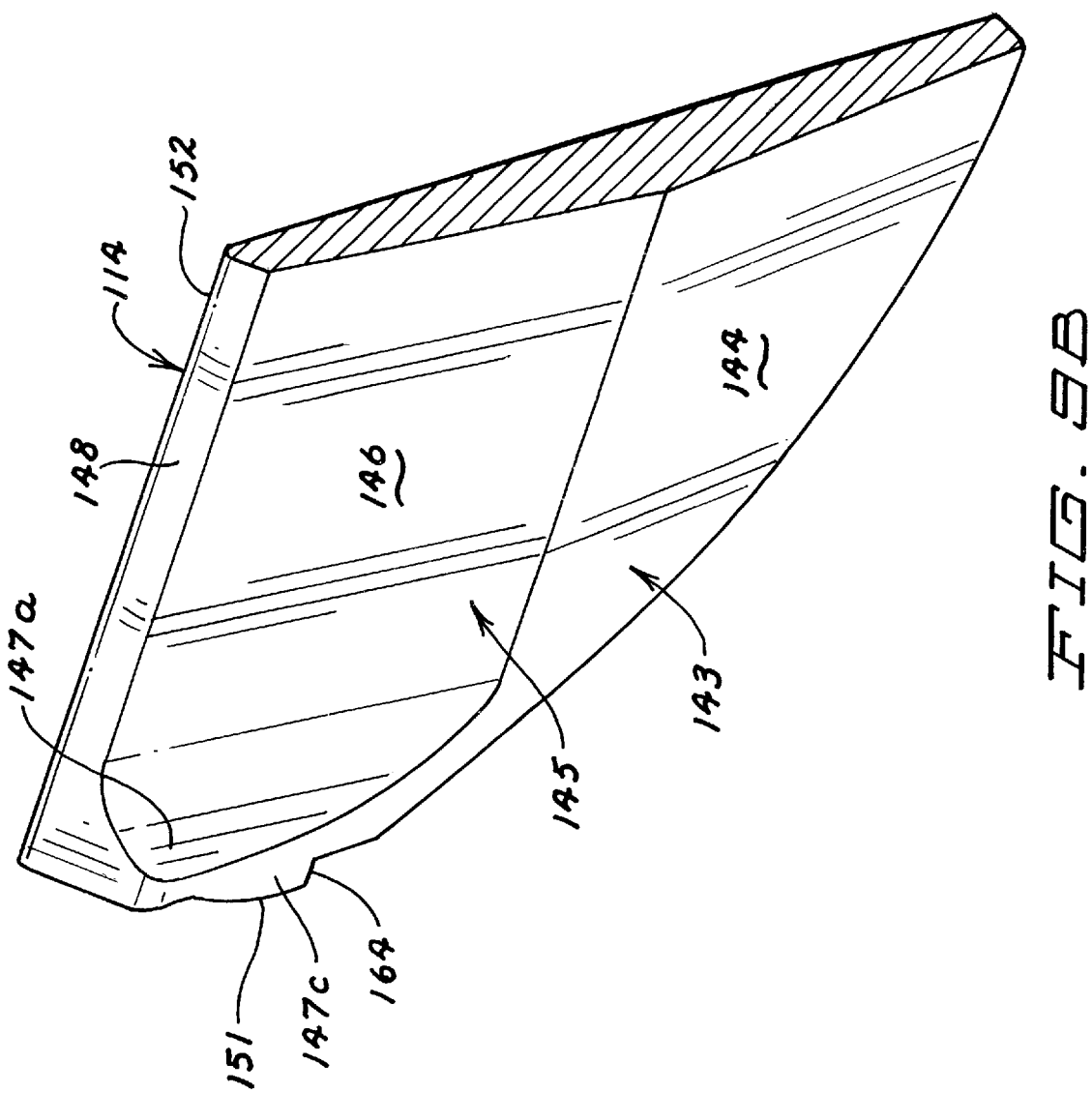

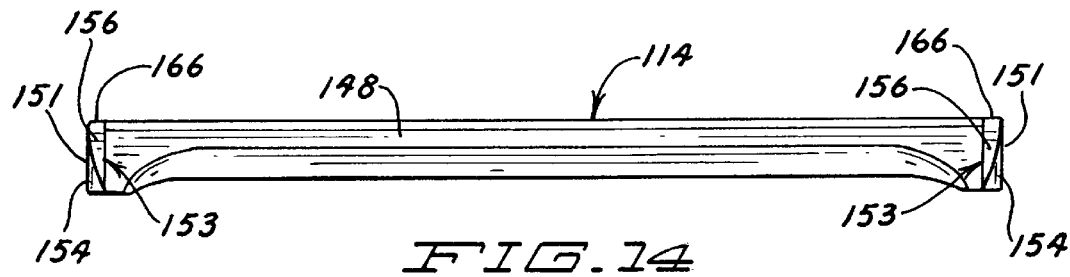
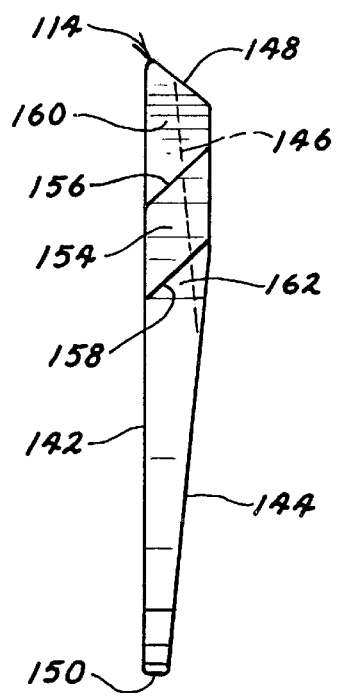 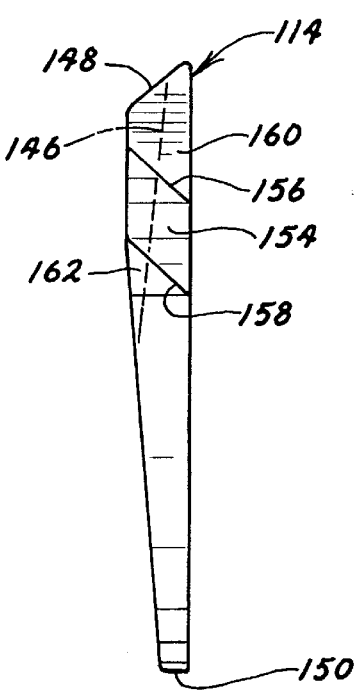
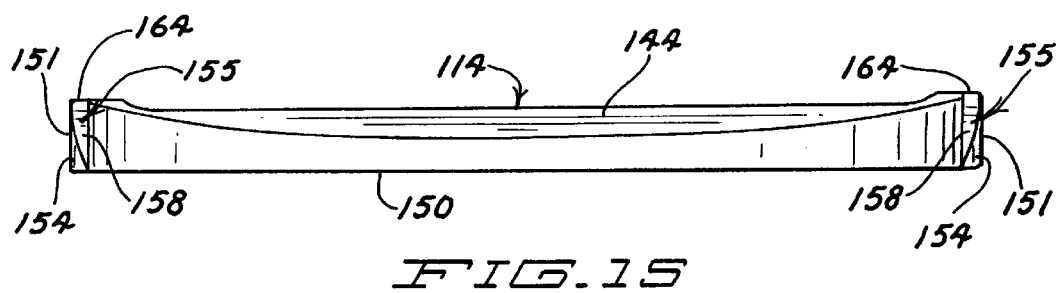

BILEAFLET HEART VALVE HAVING OPEN CHANNEL AND SWIVEL PIVOTS

CO-PENDING APPLICATIONS

The present application claims priority to U.S. Provisional application Ser. No. 60/060,922, filed Oct. 3, 1997, and relates to U.S. patent application Ser. No. 09/143669, filed Aug. 31, 1998, now abandoned which is a continuation of U.S. patent application Ser. No. 08/626,170, filed Mar. 29, 1996, now U.S. Pat. No. 5,824,062, which is a continuation-in-part of both U.S. patent application Ser. No. 08/412,696 filed Mar. 29, 1995, now abandoned, and U.S. patent application Ser. No. 08/546,210 filed Oct. 20, 1995, now abandoned, each of which is entitled BILEAFLET HEART VALVE.

FIELD OF THE INVENTION

The present invention relates generally to bileaflet hemodynamic heart valve prostheses of the type permitting translational and rotational movement of the leaflets, and particularly to a low-excursion prosthetic heart valve suitable for mitral valve replacement involving preservation of the papillary muscle and chordal structure wherein the valve may be oriented in either an anatomical or anti-anatomical configuration.

BACKGROUND OF THE INVENTION

The replacement of defective heart valves with hemodynamic prostheses is the most prevalent course of treatment for certain types of heart disease and dysfunction affecting the atrioventricular valves—namely the right AV (tricuspid) and the left AV (bicuspid) valves. Although a variety of tissue and prosthetic heart valve mechanisms have been developed, monoleaflet (tilting disc) and bileaflet valves currently hold the greatest measure of acceptance among practitioners. These valves include one or two pivoting leaflets or occluders retained within a seating collar or suture ring that is implanted in place of the physiological valve.

Replacement of a bicuspid (mitral) valve using a procedure that preserves portions of the papillary muscle and chordal apparatus is discussed herein for exemplary purposes. In that procedure, the anterior leaflet is bisected and detached from the annulus, and the two halves are groomed and then sutured to the posterior mitral annulus with the papillary muscle and chordal apparatus substantially intact. Such a procedure and its benefits are described in significant detail by H. Feikes, et al., *Preservation of All Chordae Tendineae and Papillary Muscle During Mitral Valve Replacement with a Titling Disc Valve*, 5 J. Cardiac Surg., No. 2 pp. 81–85 (1990). The authors conclude that this mitral valve replacement procedure can be practical using both monoleaflet and bileaflet valves. However, it is readily apparent to those skilled in reconstructive cardiac surgery that selection of a suitable valve type and proper orientation of the prosthesis can be important factors impacting the long term success of this procedure for a given patient. In particular, due to the position at which the valve tissue is sutured to the posterior mitral annulus, care must be taken to ensure that the peripheral edge of a leaflet does not contact the tissue during normal operation of the valve. Such contact can result in the intermittent, partial, or complete malfunction of the valve, as well as damage to or dislodgement of the valve tissue.

Four primary combinations of valve types and orientation are considered, as diagramed in FIGS. 25–28 herein. The four combinations ranked by ascending level of risk include: (1) monoleaflet valve M with anterior orientation (FIG. 25); (2) bileaflet valve with anti-anatomical orientation (FIG. 26); (3) bileaflet valve with anatomical orientation (FIG. 27); and (4) monoleaflet valve M with posterior orientation (FIG. 28). While the monoleaflet with posterior orientation is generally regarded as a high risk configuration and the monoleaflet with anterior orientation is considered to have little or no risk, the degree of risk associated with a bileaflet valve oriented in either the anatomical or anti-anatomical configuration depends upon the particular type of valve selected (particularly its range of excursions, radial exposure, and lateral exposure), the post-procedure anatomical characteristics of the annuls, and the patient's requirement for certain operational parameters associate with the valve.

While a monoleaflet valve may be preferred in order to achieve the lowest risk level with an anterior orientation, a physician may prefer to implant a bileaflet valve to obtain specific functional benefits associated with or unique to the particular bileaflet valve structure.

The bileaflet valve has been extensively developed and refined. However, there is still room for further improvement. Problems associated with the weakening or structural failure of critical components in the valve are linked both to dynamic mechanical stresses and cavitation. It is noted that a certain amount of antegrade and retrograde leakage is generally anticipated. However, the amount of leakage is preferably maintained within acceptable limits corresponding roughly to normal anatomical valves. In addition, minimizing the physical size of the valve prosthesis, particularly the longitudinal dimensions of the annular base, produces greater excursion along the peripheral edges of the leaflets, while simultaneously increasing the difficulty in raising the heights of the pivot axis. Furthermore, recesses, crevices, corners, and obstructions required to restrain the leaflets within the annular base and maintain pivotal movement also interfere with circulation, create turbulence, and produce zones of stagnation, each potentially providing a thrombogenic nidus that may eventually lead to an embolism. Although bileaflet valves are hemodynamic, spacing the fixed axis of rotation of the leaflets significantly apart from the secondary natural axis of rotation limits the maximum speed or angular rate which the leaflets may attain during opening and closing.

In regard to the selection of suitable materials, there is an inherent balancing between the selection of materials for ease of fabrication, biocompatibility, strength, and weight versus selection with respect to the acceptable level of fragility of the resulting components, particularly those involving delicate structures such as wire guides, cages, and pins that bear significant loads. In addition, the structure of many pivot mechanisms requires the annular bases to have opposing flat sides rather than a substantially or completely circular bore, thereby restricting the maximum flow volume and increasing the valve's nominal fluid pressure.

U.S. Pat. No. 4,276,658 to Hanson provides a representative example of a conventional bileaflet heart valve. That valve utilizes a pair of semicircular pivot "ears" disposes on opposing sides of each leaflet received within "hourglass-shaped" slots to control the pivotal movement of the leaflets—including the angular sweep between the open and closed positions, the tiling of the valve away from its restrained pivotal axis, and the translational movement of the leaflet both parallel with its normal plane and along the linear flow path through the bore of the annular base. The Hanson '658 patent also describes the use of a pyrolytic carbon coating over a metallic or synthetic substrate for fabrication of the valve's components.

For comparison, U.S. Pat. Nos. 4,240,161 to Huffstutler and 3,859,668 to Anderson provide representative examples of the features, structure, and operation of monoleaflet or "titling disc" heart valves.

Various improvements directed toward correcting the deficiencies described above have been developed, each achieving varying degrees of success and accompanied by inherent tradeoffs with other beneficial features.

U.S. Pat. No. 3,903,548 to Nakib discloses an effort to utilize the beneficial features of the monoleaflet principle in a bileaflet valve that similarly omits fixed pivotal axis, however the resulting cage structure produces an unacceptably small effective bore and correspondingly high pressure gradient across the valve.

In a bileaflet valve structure such as disclosed in the Hanson '658 patent, the leaflets may each pivot filly between the open and closed portions on the order of 80,000–120,000 times per day given a standard pulse of 60–80 beats per minute. Movement of the leaflets through a viscous aerated fluid such as blood may produce significant cavitation —the formation of partial vacuums caused by sudden movement of the flowing fluid away from the surface of the leaflets as a result of mechanical forces exerted by the leaflets. These partial vacuums produce "micro bubbles" on or near the surface of the leaflets, and when the pressure is released, vacuums change into positive pressure regions which lead to implosion of bubbles which can cause pitting of the surface of the leaflet. The cavitation potential is amplified greatly by the virtually instantaneous stopping and starting of the leaflets as they contact a rim along the annular base and also, in the case stopping, by the rate of speed at which the leaflet is traveling when it stops. Contact between the leaflet and the rim greatly increases the compressive forces on the adjacent fluid, and as the leaflet pivots away from the rim the corresponding effects of the expansions are magnified by increased negative pressures and stronger partial vacuums. Whereas standard cavitation produces pitting of metal surfaces due only to mechanical contact between the flowing fluid and moving object, introducing reciprocal movement and mechanical contact within the fluid cause the collapsing cavitation bubbles to strip or shear material from the leaflet surfaces at an accelerated rate. Although the surface pitting occurs at a near microscopic level, the result is surface degradation of the leaflet which can induce stress fractures and fragmentation leading to the premature failure of a leaflet.

U.S. Pat. No. 4,078,268 to Possis discloses a substantially circular bore through the annular base, as well as a nearly complete separation between the peripheral edges of the leaflets and the annular base around the circumference of the valve. While this design obviates certain cavitation problems, it permits high levels of antegrade and retrograde leakage and places the entire load of restraining each leaflet on a pair of pivot pins received within adjustable bearing plugs. The combination of increased torque, absorbed impact forces, vibration, and normal frictional contact are believed to exert undue mechanical stresses on the relatively delicate pivot pins and bearing plugs.

U.S. Pat. No. 5,080,669 to Tascon discloses an annular base that defines channels which intersect the pivot axis of the leaflets at various angles to direct flow of blood around enlargements in the leaflets that serve as the pivot axis, in an effort to cleanse the surfaces of the enlargements and prevent zones of thrombogenic stagnation from forming. However, the inward projections forming the channels and barriers restraining the leaflets in the Tascon '669 design create obstacles to uniform blood flow through the bore of the annular base, and define acute corners and crevices which can accelerate the formation of a thrombus. In addition, the enlargements continuously block a majority of the potential flow through each of the channels, thereby minimizing any cleansing effect that is realized.

U.S. Pat. No. 4,892,540 to Vallana discloses a pair of vertical "chimneys" defined by the lobes of the annular base and communicating with the recesses in which the ears of the respective leaflets are received. In concept, blood flow in either the antegrade or retrograde direction passes between the pivot ears and the side wall of the annular base to cleanse the recess. However, the angled base portions forming each wedge-shaped separator body hold the pivot ears and leaflets in an elevated position proximate to the inlet from the chimney into the recess, thereby minimizing flow through the chimney. The pivot ears either reduce the flow rate within the recess or divert the flow away from portions of the recess where stagnation could occur, thus diminishing the effectiveness of any cleansing action. Whereas Tascon '669 contemplates alternating between multiple flow paths oriented at diverse angles to enhance the "scrubbing" effect, Vallana '540 only contemplates cleansing that is substantially repetitive and reciprocal along one path for both antegrade and retrograde flow. Finally, to the extent that Vallana '540 would produce an acceptable retrograde cleansing action due to the pressure differential created within the recess feeding into the chimney, it is at the expense of a significantly restricted non-circular bore through the annular base accounting for a substantial reduction in antegrade circulation.

Although the Hanson '658 patent discloses the pivot ears preventing blood stagnation in the area of engagement with the recesses, the use of transesophageal echocardiography in patients receiving mitral valve replacements has shown the formation of dangling fibrin strands along the interior surface of the valve in the areas between and proximate to the pivot recesses. These small filamentous abnormal echoes (SAE) are considered non-obstructive while within the valve, however their frequent disappearance strongly suggests a thrombotic origin and a significant correlation with the risk of early thrombogenic episode has been observed.

Many factors may be responsible for the formation of the fibrin strands, including regions of blood stagnation which provide a nidus for thrombogenic formations, or defects in the materials or structure of the valve that permit the direct attachment of blood cells. It may therefore readily be appreciated that two important goals when designing a bileaflet heart valve are maintaining optimal antegrade and retrograde circulation, and eliminating regions of reduced circulation within the valve that might foster the development of a thrombogenic mass. It is suggested that while the Hanson '658 patent shows a relatively shallow semi-circular recess, in practice it has not been possible to achieve a workable commercial embodiment of a bileaflet valve having pivot ears with a suitably shallow recess to enhance cleansing of the recess by normal antegrade and retrograde circulation. For example, the commercially available embodiments of the Hanson '658 valve have recesses forming entrance angles ranging from 35° to 48° measured between the lateral wall of the bore and the tangentially adjoining surface of the recess, depending upon overall size of the valve. Recesses forming an angle of 35° or less with the adjoining lateral wall have been achieved in monoleaflet valves, however the significantly different structure and operation of monoleaflet valves has not permitted the successful utilization of many comparable features in bileaflet valves.

Various adaptations have also been made in an effort to improve the pivot mechanism. One option is to eliminate the pivot ears or pins, and allow the leaflet to rock on projections extending inwardly from the annular base. These configurations generally require some engagement between the leaflet and the projections—either the projection being received within a notch or recess in the leaflet, or the leaflet forming a trapping flange that prevents egress from between two spaced-apart projections. For example, U.S. Pat. Nos. 4,863,459 to Olin and 4,935,030 to Alonso describe leaflets that include a swelled area or camming surface trapped between two projections. U.S. Pat. Nos. 4,373,216 to Klawitter, 4,692,165 to Bokros, 4,872,875 to Hwang, and 5,354,330 to Hanson each describe a variation in which the leaflet defines a peripheral notch or recess receiving a projection the annular base. While designs utilizing a notch in the leaflet are more secure than the trapped flange configurations, they are also more difficult to assemble without placing undue stress on the leaflets or projections. In addition, these designs similarly present flat-sided bores and projections which extend into the bore and obstruct antegrade flow. As the complexity of these projections increases, the opportunity for a crevice or recess providing a thrombogenic nidus also increases. Representative examples of relatively complex pivot structures that present several potential stagnation sites include U.S. Pat. Nos. 5,116,367 to Hwang and 5,123,920 to Bokros.

One prominent feature of the bileaflet valves discussed above is the degree of exposure or incursion that is exhibited by the leaflets relative to the annular base. Excursion can be thought of as the maximum distance which the distal ends of the leaflets protrude from the bottom of the annular base when the valve is completely open, measured from the lowermost planar surface of the base to the most distal point on the peripheral edge of the respective leaflet. However, when comparing the anatomical and anti-anatomical orientation of a bileaflet valve with reference to the mitral valve replacement procure discussed above, incursion can also encompass two more complex relationships.

U.S. Pat. Nos. 5,246,453 to Bokros and 5,002,567 to Bona disclose alternate configurations in which the leaflets are not generally planar, and are supported by and pivot about fulcrums disposed on the lower portion of each leaflet. While these designs present an incursion both above and below the annular base, it allows the height of the annular base to be reduced somewhat relative to comparable bileaflet valves. While such a design is considered to be more responsive to reversal in the antegrade flow, it also relies upon shifting the axis of rotation relative to the leaflet's moment of inertia and therefore produces different operational characteristics than might normally be expected.

One factor previously alluded to which affects the speed at which the valve operates, is the displacement between the fixed axis of rotation and the corresponding En moment of inertia of the leaflet. Another factor is the shape of the leaflet. In this regard, optimization of several physical parameters must be contemplated. The leaflets must move through an arcuate path in response to fluid pressure applied from both the antegrade and retrograde directions, starting from differential initial orientations relative to the fluid pressure, and within an initially static versus initially dynamic environment. Consequently, valves having superior opening characteristics may be slow to close or resist complete closure, and vice versa. Leaflets having an angled, curved, or bicurved design to enhance the immediate responsiveness to changes in hemodynamic forces can be employed to address this problem. Other factors include reducing turbulence or backwash that might resist the leaflet's momentum or increase its apparent resting inertia, reducing the weight or thickness of the leaflet, allowing the leaflet to rock or cam differently in response to antegrade or retrograde pressures, maximizing the laminar flow through the valve body over the entire leaflet surface, and eliminating sources of friction, vibration, or misalignment that could adversely affect the mechanical operation of the valve.

Another approach mentioned above is to increase the translational movement of the leaflet within the annular body, thereby permitting the leaflet to pivot more naturally about its inertial axis in direct response to the hemodynamic forces. This approach can potentially be more beneficial than merely moving the fixed axis of rotation nearer to the moment of inertia, since it also serves to reduce frictional forces and other physical impediments to proper valve operation. One limitation is the need to maintain proper alignment and seating of the leaflet without encumbering the flow passage with obstructions or incorporating free structures that increase the likelihood of valve failure.

U.S. Pat. No. 4,535,484 to Marconi describes a bileaflet valve in which the leaflets are "free-floating", thereby increasing translational movement and reducing the mechanical stresses imposed at localized pivot points and other load bearing surfaces. However, the Marconi '484 design requires a complex and fragile cage structure to restrain the leaflets, thereby producing a significant risk of damage to the valve during manufacturing or handling and increasing the potential for catastrophic failure of a valve component that would result in death or severe injury to the patient, mitigating against the use of certain materials such as pyrolytic carbon, and greatly increasing the cost and complexity of fabrication.

For comparison, U.S. Pat. No. 4,689,046 to Bokros describes a trapezoidal pivot ear having beveled edges, arguably decreasing the translational freedom, but enhancing the "sweeping" effect of the pivot ear to prevent thrombogenic formations within the recesses and distributing lateral stresses over a wider surface area.

It will also be appreciated from analyzing bileaflet heart valves, such as disclosed by the Hanson '658 and Possis '268 patents, that the leaflets divide the bore into three passages having unequal cross-sectional areas, and that corresponding effects on fluid dynamics should be expected. Observation of these valves in operation shows that flow rates through the passages will vary generally inversely with the corresponding cross-sectional area. As such, in a valve such as Hanson '658 which present a relatively narrow central passage, the flow rate of blood passing through that central passage is greater than through the two passages on opposing sides. The faster blood flow in the center, relative to the sides, can cause additional turbulence within or downstream of the valve, or produce a pressure differential or venturi effect within the valve that can impede or retard the optimal translational or pivotal movement of the leaflets. The Possis '268 valve presents a larger central passage with narrower cross-sectional passages on each side, thereby reversing the fluid dynamics compared with the Hanson '658 design.

While many common functional goals have been recognized among designers of bileaflet heart valve prostheses, there are strongly divergent opinions concerning the prioritization of those goals and how best to achieve specific results or advantages. Accordingly it will be readily appreciated that these competing factors significantly influence the design and optimization of all bileaflet heart valves and that further improvements may be made. The present invention provides advantages over the prior art bileaflet heart valves and solves problems associated therewith.

SUMMARY OF THE INVENTION

Briefly described, the bileaflet heart valve prosthesis of the present invention comprises an annular base defining a substantially circular bore, and a pair of pivoting leaflets; each of the respective leaflets having first and second sides, the first side being a top side and the second side being a bottom side, the bottom sides of the respective leaflets generally facing one another when the respective leaflets are in an open position; each bottom side having an upper half and a lower half, a major portion of the upper half providing an upper surface lying generally in a first plane and a lower half providing a lower surface lying generally in a second plane, the first plane lying at an angle to the second plane; a third plane passing through a horizontal cross-section of the annular base, the first and second planes lying at angles to the third plane when the leaflets are in either the open or closed positions; wherein the first plane of each of the respective leaflets extends beyond an angle of 90° with respect to the third plane when the leaflets go from the fully closed position to the fully open position.

The first plane can extend beyond a 90° angle with respect to the third plane when the leaflets go from the fully closed position to the fully open position without diminishing the leverage for closure of the leaflets when the leaflets are in the fully open position. This is because the lower portion of the bottom side of the leaflets remain at a suitable angle to allow for adequate leverage against the lower portion of the leaflet, to shift the leaflets within the respective recesses and pivot the leaflets to the closed position once the upper fulcrum edge comes into contact with the upper sidewall of the respective recess.

In preferred embodiments the leaflets have a beveled bottom side which minimizes the travel angle "k'" between the open and closed positions. The lateral ends of each leaflet are received within "open channel" recesses where the ends are "free floating", permitting translational and rotational movement of the leaflets within the respective recesses. In preferred embodiments, each recess communicates with at least one groove extending around an inner peripheral surface of the annular base, and a cleansing flow is directed vertically or angularly through the recess to the groove during antegrade circulation, and from the grooves through the recess during retrograde flow and valve closure. The direction of this cleansing flow through the recesses varies depending upon the direction of circulation and the orientation of the leaflets, and is mostly unobstructed within the recesses by the leaflets. The peripheral edges of the leaflets present minimal incursion or exposure beneath the bottom of the annular base when the valve is completely open. When the leaflets of the valve are closed, the peripheral edge of each leaflet in the central region is preferably slightly spaced apart from the annular base to allow free movement of the leaflet and to avoid unsuccessful wear and/or stress. The peripheral edge of each leaflet in preferred embodiments only contacts the annular base adjacent the groove proximate the lateral regions of the leaflet.

In preferred embodiments, the angle at which fluid washing the surfaces of the annular base flows into the recesses is less than 35° to permit better washing dynamics. The preferred valve also has a dynamic pivot constructed primarily on the lateral sides of the leaflets where two fulcrum edges are created by notches in the peripheral edge. The leaflets pivot on each of the respective fulcrum edges at different points in the opening and closing cycle of the valve. This swivel pivot mechanism also permits significant translational movement of the leaflets especially in the fully open position. This mechanism is believed to provide a pivot mechanism which permits the valve to open and close more rapidly than prior art bileaflet valves.

It is one object of this invention to design a bileaflet heart valve prosthesis of the type used for tricuspid or bicuspid (mitral) valve replacement, and particularly one which provides superior operating capabilities and minimizes the risk to the patient when implanted using a procedure involving preservation of the papillary muscle and chordal structure by fixation to the posterior mitral annulus.

It is a related object of this invention to design the above bileaflet valve for implantation in either the anatomical or anti-anatomical configuration, such that the peripheral edges of the leaflets present an extremely low incursion below the bottom surface of the annular base, and further present minimal radial and lateral exposure.

It is an additional object of this invention to design the above bileaflet valve such that the passages through the bore of the valve between the leaflets provide substantially equal relative flow rates, thereby mitigating against flow differentials, gradients, or venturi effects which would otherwise cause turbulence or impede the translational or pivotal movement of the leaflets.

It is another object of this invention to design the present bileaflet valve such that it utilizes a "free floating leaflet" configuration with no pivot ears or projections, to thereby reduce and redistribute mechanical or contact stresses otherwise focused on these pivot axis in conventional bileaflet valves.

It is a further object of this invention to design the above bileaflet valve such that it defines a cleansing channel or recess within the annular base in the region traversed by the lateral ends of the leaflets, and such that the cleansing channel is unobstructed within that region in a generally vertical direction, and induces or "steers" both vertical and angular fluid flow through that region during antegrade and retrograde circulation.

It is another object of this invention to provide a bileaflet valve such that a shallow angle of less than about 35° may be formed between the lateral surfaces of the annular bore and the adjoining surfaces of the recesses which restrain the leaflets. It is believed that this will enhance cleansing of the recesses by normal antegrade and retrograde circulation. Furthermore, because the recesses have unobstructed open channels permitting easy antegrade and retrograde flow through the recesses, the surfaces within the respective recesses will permit enhanced washing action.

It is a further object of this invention to provide a bileaflet valve such that the peripheral edge of each leaflet is received within a recess and beneath a seat defined by the annular base, such that there are no observable gaps between the annular base and peripheral edge in the contact regions between the leaflets and annular base when viewed from a perspective along the longitudinal axis of the valve.

It is a fisher object of this invention to design the above bileaflet valve such that the annular base of the valve defines beveled arcuate surfaces which contact the edges of the leaflets as the leaflets move between the open and closed positions, thereby creating a generally smooth and continuous arcuate path along which the leaflets roll when pivoting between the open and closed positions to distribute stress forces over an extended region of the leaflet and annular base.

The above-described features, advantages and objects, along with various other advantages and features of novelty are pointed out with particularity in the claims of the present invention annexed hereto and forming a part thereof. However, for a better understanding of the invention, its advantages, and objects attained by its use, reference should be made to the drawings which form a further part hereof and to the accompanying descriptive matter in which there is illustrated and described preferred embodiments of the present invention.

BRIEF DESCRIPTION OF THE DRAWINGS

In the drawing, in which like reference numerals indicate corresponding parts throughout the several views:

FIG. 9B is a cross-sectional perspective view of the preferred leaflet shown in FIG. 1, in a manner similar to that shown in FIG. 9A, but providing a perspective view only of a cross-section of the leaflet as seen from the line 9B–9B of FIG. 9A;

FIG. 12 is a vertical side view of a first lateral side of the leaflet of the preferred bileaflet heart valve shown in FIG. 1;

FIG. 13 is a vertical side view of a second lateral side of the leaflet of the preferred bileaflet heart valve shown in FIG. 1;

FIG. 14 is a horizontal side view of an upper edge, including the mating edge, of a leaflet of the preferred bileaflet heart valve shown in FIG. 1;

FIG. 15 is a horizontal side view of the peripheral edge of the leaflet of the preferred bileaflet heart valve shown in FIG. 1;

DETAILED DESCRIPTION OF THE PREFERRED EMBODIMENTS

Figure 1:
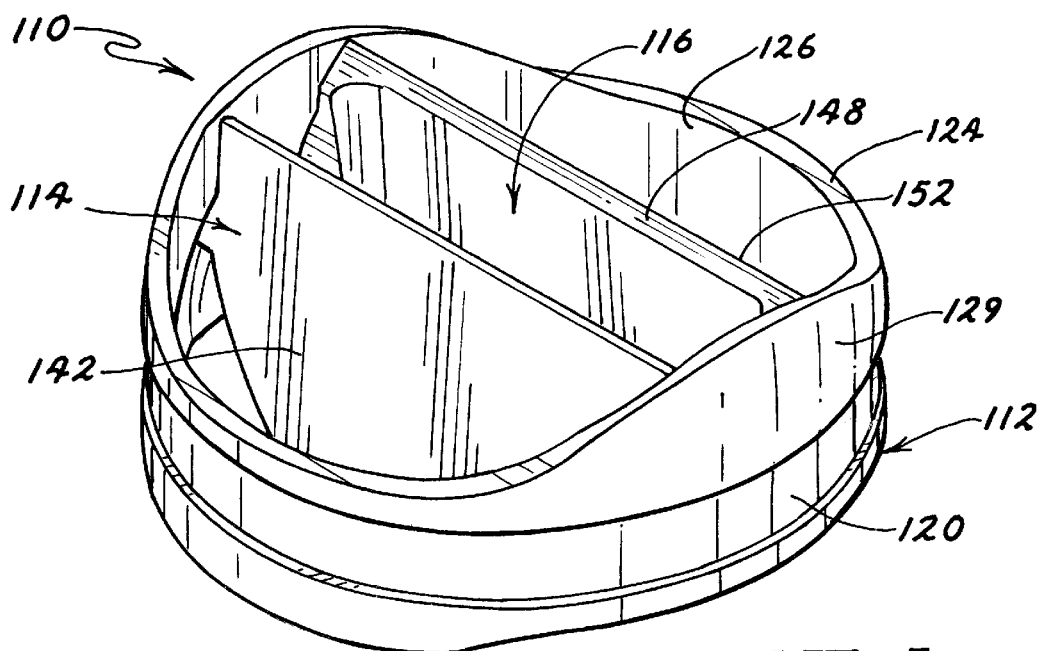
FIG. 1 is a perspective view of a preferred embodiment of the present invention showing the leaflets in a fully open position.
Figure 2:
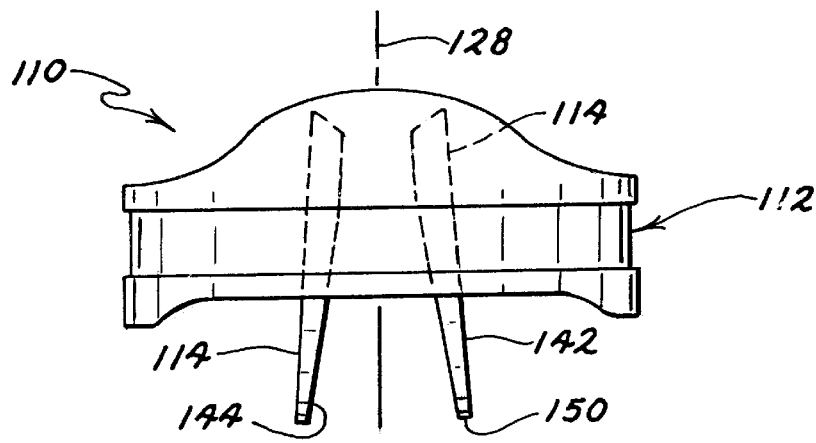
FIG. 2 is a lateral side view of the preferred bileaflet heart valve of the present invention shown in FIG. 1.
Figure 3:
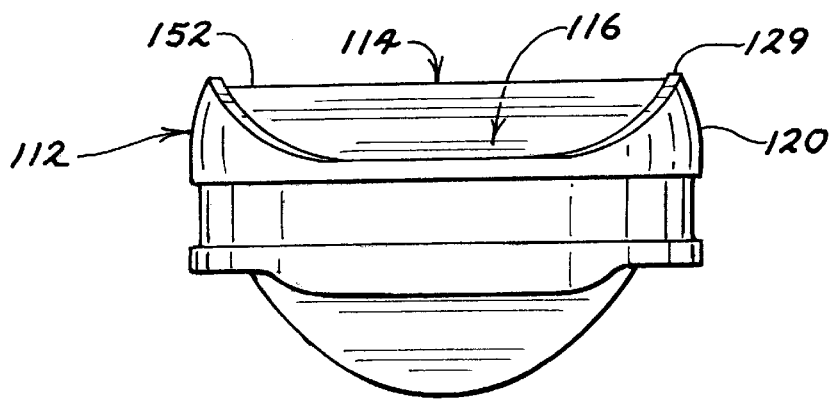
FIG. 3 is a lateral side view of the preferred bileaflet heart valve shown in FIG. 1.
Figure 4:
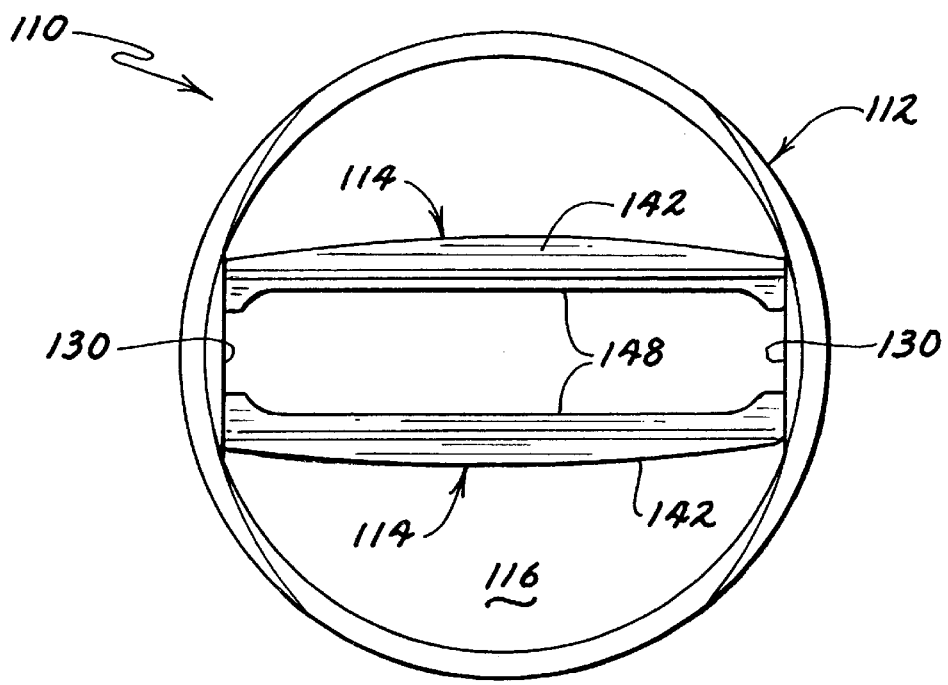
FIG. 4 is a top plan view of the preferred bileaflet heart valve shown in FIG. 1.
Figure 5:
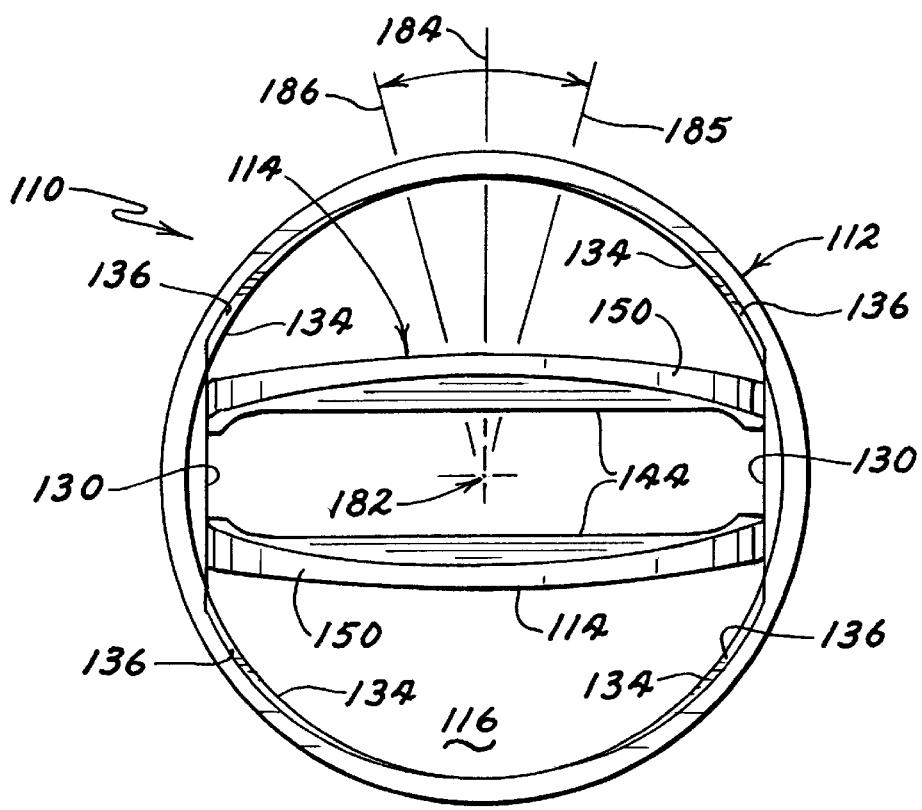
FIG. 5 is a bottom plan view of the preferred bileaflet heart valve shown in FIG. 1.

Referring now to the drawings, a preferred bileaflet heart valve prosthesis 110 of the present invention and parts thereof are illustrated. The bileaflet heart valve prosthesis 110 of the present invention is preferably fabricated from a metal such a titanium, a carbon compound (or carbon with a minor percentage of silicon) such as pyrolytic carbon or the like, a metal alloy, or a suitable substrate coated with pyrolytic carbon as are well known in the art.

Figure 26:
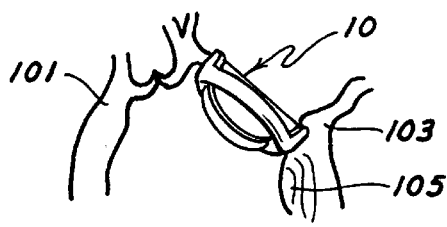
FIG. 26 is a perspective view of a bileaflet heart valve with anti-anatomical orientation.
Figure 27:
FIG. 27 is a perspective view of a bileaflet heart valve with anatomical orientation.
Figure 28:
FIG. 28 is a perspective view of a monoleaflet heart valve with posterior orientation as known to the prior art.
Figure 29:
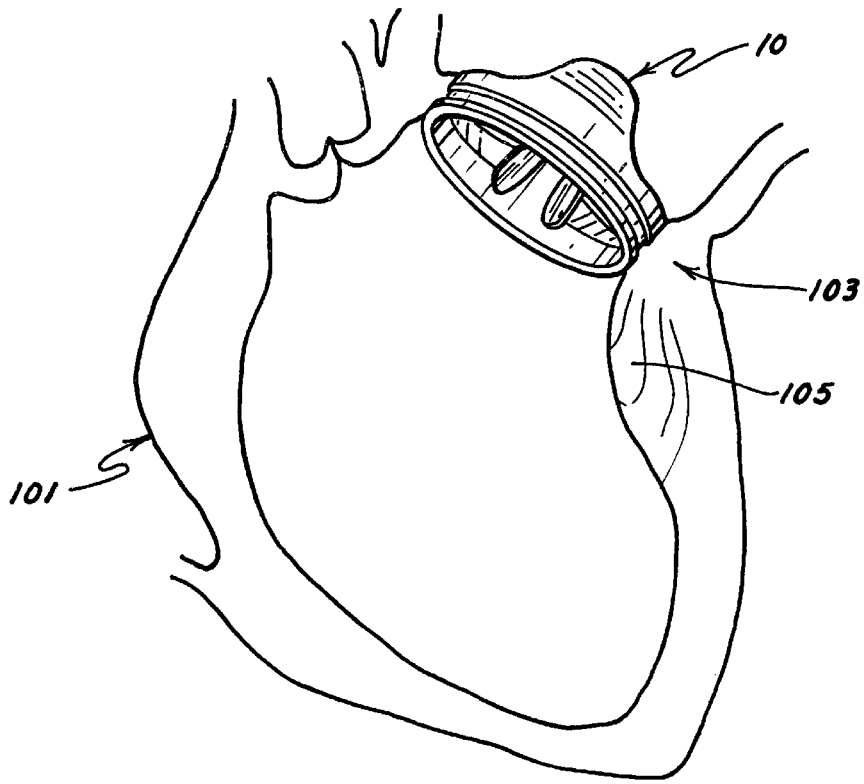
FIG. 29 is a perspective view of a bileaflet heart valve of the present invention implanted in an anatomical orientation.

Referring now to FIGS. 25–29, a bileaflet heart valve 10 similar to the preferred heart valve prosthesis 110 of the present invention is shown diagrammatically implanted within the heart 101 of a patient, with the valve 10 sutured in place proximate to the mitral annulus 103 of the anatomical coronary valve and disposed above the papillary muscle and tendineae chordae 105 fixed to the posterior mitral annulus as described previously. The bileaflet valve 10 may be implanted in either the fully anatomical orientation or the fully anti-anatomical orientation as shown in FIGS. 26 and 27, respectively, or adjusted between the fully anatomical and anti-anatomical orientations by rotating the valve 10 within the corresponding suture ring (not shown) as is well known to the art. These orientations may be compared with the anterior and posterior orientations of a monoleaflet valve M shown in FIGS. 25 and 28.

Referring now to FIGS. 1–5, a preferred embodiment of the bileaflet heart valve prosthesis 110 is described. The preferred bileaflet heart valve 110 of the present invention shown in FIG. 1 includes an annular base 112 and first and second leaflets 114. The fist and second leaflets 114 are mounted within the annular base 112 for pivotal movement between a fully open position, shown in FIGS. 1–5 and diagrammatically in FIG. 16, and in phantom in FIG. 17, and in a fully closed position shown in FIGS. 22–23 and diagrammatically in FIG. 17. Referring now also to FIGS. 68, the annular base 112 has a top surface 124 and an inner wall 126 which defines a generally circular bore 116 passing through the annular base 112 in a direction generally parallel with a longitudinal axis 128 oriented generally in parallel with a vertical path for circulation of fluid or blood through the generally circular bore 116.

The top surface 124 of the annular base 112 is raised proximate opposing lateral sides 129. On the inner wall 2 inner surface sidewall 126 of the annular base 112 proximate the opposing lateral sides 129, are flat portions 130 of lateral surfaces 133 which define flat lateral sides of the generally circular bore 116. The flat portions 130 of the lateral surfaces 133 include a pair of recesses 132 in each of the respective lateral sides 129 of the base 112. Further lateral depressions 135 are centrally located in a lower portion of the inner surface 126 proximate each of the two lateral sides 129, below and between the respective recesses 132 on each side, in the respective flat portions. In preferred embodiments, these depressions have a curvilinear surface which would define a portion of one side of a cone. The recesses 132 extend into the respective flat portions 130 of the lateral surfaces 133, thereby displacing a cylindrical bottom surface 140 of the recess 132 from the respective lateral surface 133 proximate the respective lateral side 129. In preferred embodiments of the present invention, each of the cylindrical bottom surfaces 140 of the respective recesses 132 pass through a cylindrical radius which is "feathered out" as the cylindrical surface 140 approaches a junction with the respective lateral surface 133.

Figure 19:
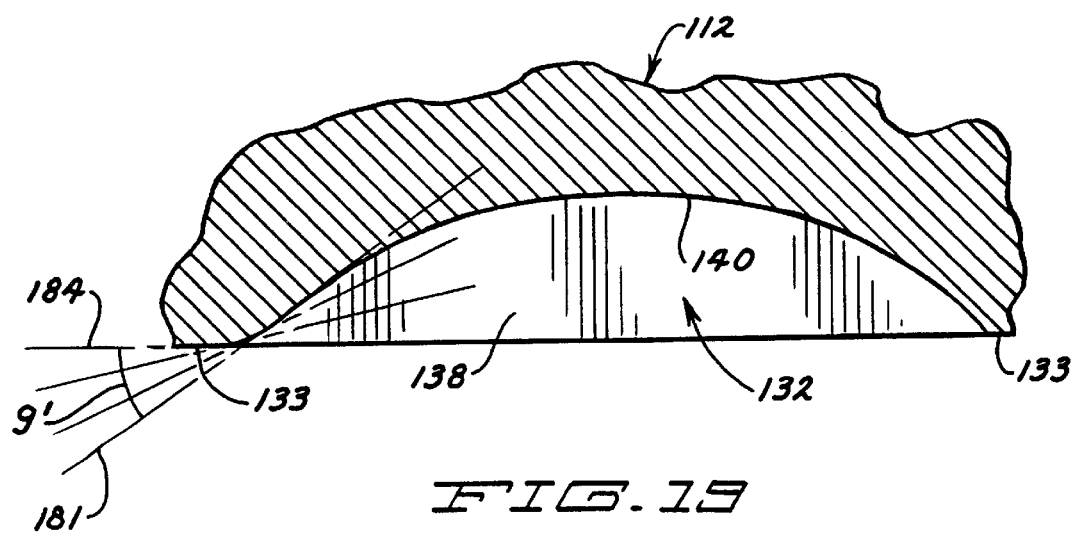
FIG. 19 is a partially broken away cross-sectional view of the recess as seen from the line 19—19 of FIG. 7.

Referring now also to FIGS. 18–21, a line 181, shown in FIG. 19, which is tangential with a point on the cylindrical bottom surface 140 of the recess 132 just prior to a further point at which the cylindrical surface 140 is "feathered out" to form a junction with the lateral surface 133, lies at an angle "g'" to a tangent line 184 which intersects line 181 and is tangential to the lateral surface 133. In order to properly measure the entrance angle "g'" to the recess 132, a number of lines similar to line 181 which are tangential to a point on the cylindrical surface 140 must be considered. This may be an infinite number of lines. The entrance angle, "g'", will be the angle between the lines 184 and 181 which will be the greatest angle that exists between the line 184 and any of the lines which can be drawn which intersect with line 184 and are tangential to a point on the cylindrical surface 140. This angle "g'", is representative of a recess entrance angle to the cylindrical recess 132. In preferred embodiments the recess entrance angle is less than about 35°. Preferably, the recess entrance angle "g'" is between about 20° and about 35°. More preferably, the recess entrance angle "g'" is from about 25° to about 34°. In even more preferred embodiments, the recess entrance angle "g'" ranges from about 28° to about 33.5°. There is no preferred angle because the preferred angle may vary in response to changes in other parameters, especially the diameter of the annular base 112. It will be appreciated that recesses to retain pivotal leaflets have existed in the bileaflet heart valve prostheses of the prior art for some time. It is believed, however, that a lower recess entrance angle will facilitate washing of the recess to minimize stagnation and potential for thrombogenic events in proximity to the recess 132. Therefore, it is believed that diminishing the angle of entrance to the recess 132 will provide for better washing activity and lessen any potential for embolism which may exist in patients utilizing prosthetic heart valves.

Referring now also to FIGS. 9–15, the leaflets 114 have two sides, a top planar surface 142 and a beveled bottom side 143. The bottom surface 143 has a peripheral bevel portion 144 proximate the peripheral edge 150 and a central portion or central bevel 145 proximate a mating edge 148. The mating edge 148 has a narrow planar surface running nearly the entire width of the leaflet 114. The respective leaflets are mirror images of one another in preferred embodiments so that when the respective leaflets 114 pivot to reside in the fully closed position, the mating edges 148 of the respective leaflets mate together to significantly obstruct blood flow through the very limited space between the respective mating surfaces 148.

It will be appreciated that some blood will "regurgitate" between the mating edges 148 of the respective leaflets 114 when they are closed. However, this is to be expected. In fact, such blood flow, while it should be minimized, performs an important function of cleansing the mating edges 148 as the blood regurgitates between the respective edges 148.

The central beveled portion 145 of the beveled bottom side includes a flat planar surface 146 which is flanked on either side along the width W of the leaflets 114, by curvilinear side surfaces 147a and 147b which rise up proximate lateral sides 151 of the leaflets 114 to flat side bevels 147c and 147d which separate the mating edges 148 from the peripheral bevel 144 on the beveled bottom side 143 proximate the respective lateral sides 151. The width Wps of the flat planar surface 146 is greater than one-half of the width W of the leaflet 114, and is therefore a major portion of the central bevel 145. As used herein, the phrase "a major portion" means a portion of the whole which has a width dimension which is at least as great as that of one-half of the width of the whole.

The respective lateral sides 151 of the respective leaflets 114 each have a cylindrical surface proximate the diamond-shaped cylindrical surface 154. Notches 153, 155 are located adjacent to the diamond-shaped cylindrical surface 154. The inflow notches 153 are located generally between the diamond-shaped cylindrical surface 154 and the top edge of the leaflet 114. The generally V-shaped notch 153 is created and defined by an inflow flat 160 and an inflow side wall 156 of the diamond-shaped cylindrical surface 154. The generally V-shaped notch 155, called the outflow notch 155, is created and defined by an outflow flat 162 and an outflow side wall 158 of the diamond surface 154.

As previously discussed herein, washing of the various surfaces, crevices and the like by blood fluid passing through the heart valve prosthesis 110 is believed to be particularly important to reduce stagnation and potentially thrombogenic activity. The present bileaflet heart valve 110 is designed with this in mind. All of the surfaces of the present valve 110 are actively washed at one time or another in the pumping cycle of the heart in which the valve 110 is implanted. When the valve 110 is in the fully opened position all of the surfaces of the side wall 126 are actively washed by blood flowing over the surfaces, as are the recesses 132. The leaflets 114 are also actively washed as the blood flows in the antegrade direction through the bore 116.

Figure 22:
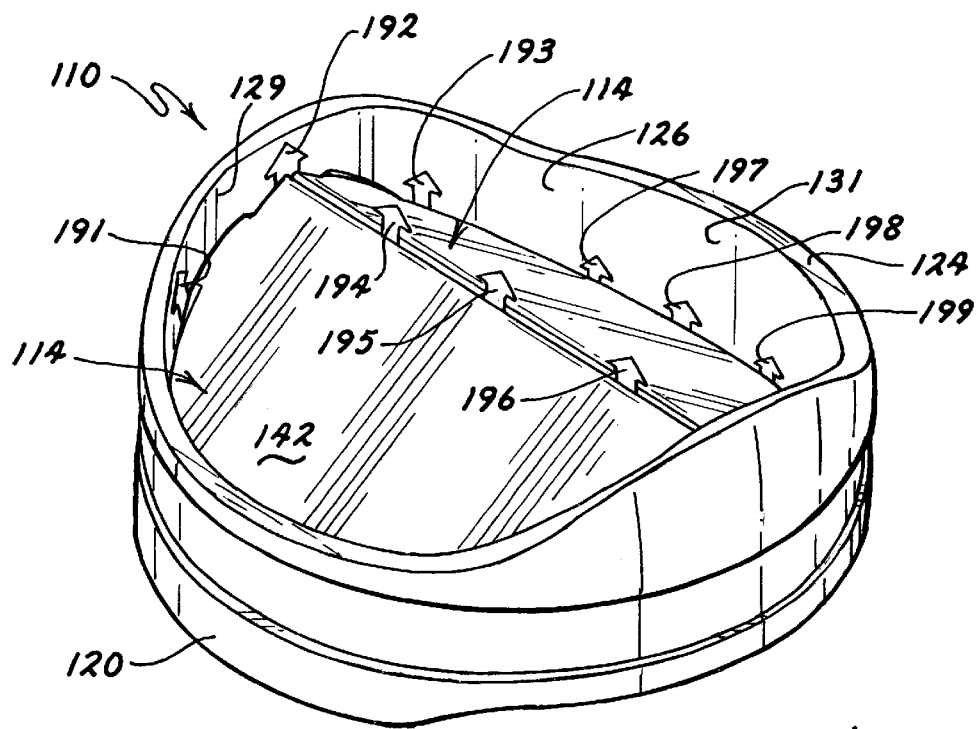
FIG. 22 is an elevated perspective view of the preferred bileaflet heart valve of the present invention similar to that shown in FIG. 1, except that the leaflets are in a fully closed position.

The diamond-shaped cylindrical surface 154 also has a cylindrical radius generally consistent with the cylindrical radius of the bottom surface 140 of the recess 132. As shown particularly in FIG. 22, when the leaflets 114 are in a fully closed position, some regurgitation of blood through the bileaflet valve 110 occurs in the retrograde direction. The regurgitation is desirable to a certain degree, so long as the energy efficiency of the pumping activity of the heart is not compromised. The regurgitation occurs in a number of areas. Referring now also to FIG. 22, and the other illustrations of the preferred bileaflet heart valve 110, retrograde blood flow may pass between the mating surfaces 148 of the respective leaflets 114 as demonstrated by arrows 194, 195 and 196 in FIG. 22. The bottom of the leaflets 114 also channel retrograde blood flow into the recesses 132 by directing the blood against the seats 136 created by the separation between the cylindrical bottom surface 140 and the upper edge 134 of the recesses 132. An outflow side wall 158 of the diamond surface 154 may also channel retrograde blood flow to the recesses 132 and particularly to the seat 136. This flow will then regurgitate between the leaflet 114 and the side wall 126 after it flows over the seat 136 and come out proximate the regurgitation representation arrows 191, 192 and 193. It will be appreciated that flow through areas where the top planar surface 142 meets the seat 136 will be minimized and that this flow can be further minimized by widening the seat 136 further into the transverse side 131. Additional retrograde blood flow will wash other portions of the valve 110, especially portions of the inner wall 126, including the lateral depressions 135 and the flat portions of the lateral surfaces 133, and channel upwards proximate arrow 192 in FIG. 22. It will be appreciated that there will almost always be at least some separation between the peripheral edge 150 of the leaflet 114 and the side wall 126. This enables retrograde blood flow to regurgitate between the peripheral edge 150 and the side wall 126 proximate the entire peripheral edge 150. Even where the top planar surface 142 of the respective leaflets 114 are pressed against the respective seats 136, there is at least some space between the opposing surfaces for a very limited amount of "regurgitating" retrograde blood flow. The regurgitation is particularly significant proximate the transverse sides 131. This is particularly true because of the side wall surface 126 proximate the center of the peripheral edge 150 is flush, thereby providing no obstruction to the retrograde flow of blood. It will be appreciated that the seat 136 is fully diminished to nothing in this area in preferred embodiments. A further discussion of the seats 136 follows a further description of the leaflets 114 immediately below.

Referring now particularly to FIGS. 16–21, a certain amount of "play" exists between the respective surfaces in the area of the diamond surface 154 and the recess 132 when the leaflets 114 are in the open position. This "play" permits a significant amount of translational movement. Because of the increased potential for translational movement between these surfaces when in the open position, the leaflets 114 have greater freedom for translational motion than is either exhibited or generally possible in any of the prior art valves which have "matched" or "parallel" surfaces in both the open and closed positions. As shown diagrammatically in FIG. 17, when the leaflets 114 are in the fully closed position, the top planar surface 142 is pressed against the seat 136 proximate the upper edge 134 of the recess 132. Although considerable separation appears to exist between these surfaces in FIG. 17, this separation is exaggerated for clarity. During use of the valve 110, the top planar surface 142 abuts against the seat 136. In actual fact, the spacial relationship between the top planar surface 142 and the seat 136, when the leaflets 114 are in the closed position, is that shown in FIG. 22, where the seat 136 cannot be separately called out because it is not visible in the view.

Figure 17:
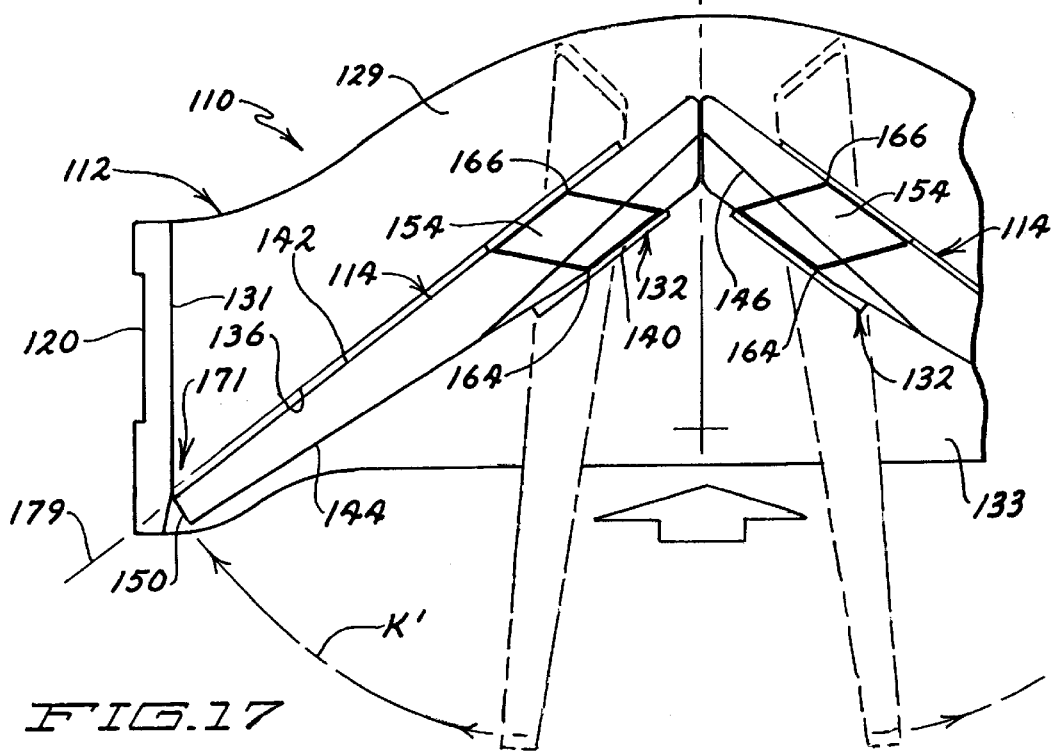
FIG. 17 is a diagrammatic cross-sectional view of the preferred bileaflet heart valve shown in FIG. 1 illustrating the transition of the leaflets from a fully open position to a fully closed position.
Figure 18:
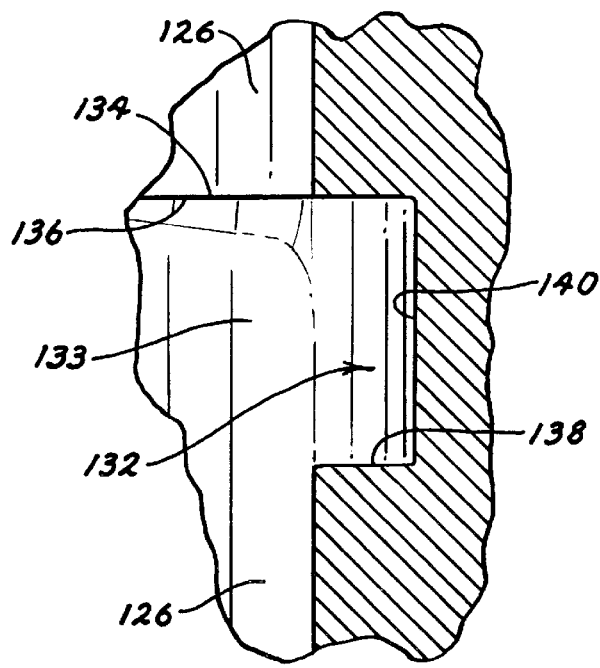
FIG. 18 is a partially broken away cross-sectional view of the recess as seen from the line 18—18 of FIG. 7.

An axis 165, parallel with respective cylindrical surfaces on diamond-shaped cylindrical surfaces 154 of the respective leaflets 114, and perpendicular the top surface 142 will lie at an angle "k" to an axis 167, parallel with the respective cylindrical bottom surface 140 of respective recess 132, and perpendicular with the upper edge 134 of the recess 132, when the leaflets 114 are in the fully opened position. When the leaflets 114 are in the fully closed position these respective axes 165 and 167 will be either superimposed upon one another, or in parallel with one another and the angle "k" will generally be about zero. In this position, therefore, the cylindrical surfaces 140 will be "matched" or "parallel" with the diamond-shaped surfaces 154 of the respective lateral sides 151 of the respective leaflets 114. The angle "k", shown diagrammatically in FIG. 17, is equal to the travel angle "k'", when the leaflets 114 are in the fully open position.

It will be appreciated that significant translational movement is permitted when the leaflets 114 are in the open position. This can be seen in FIG. 16 where the first axis 165 of the leaflet 114 lies at an angle "k" with respect to the second axis 167 of the cylindrical recess bottom surface 140. This translational movement of the leaflet 114, when in the fully open position, is believed to allow the leaflet 114 to move from its fully open position to its fully closed position much faster than prior art devices. This is because the initial movement, when a retrograde flow of fluid begins, is an upward translational movement of the diamond-shaped surface 154 within the recess 132, until the top side fulcrum edge 166 engages the upper edge sidewall or seat 136 within the recess 132. When the top side fulcrum edge 166 engages the seat 136 within the recess 132, the leaflet 114 has already overcome any inertia it may have had when "resting" in the fully opened position. The translational movement will subsequently give way to pivotal movement of the leaflet toward the fully closed position. This pivotal movement will occur rapidly since the initial translational movement will provide some momentum which will be translated into pivotal or annular movement toward closure of the leaflets 114.

Figure 20:
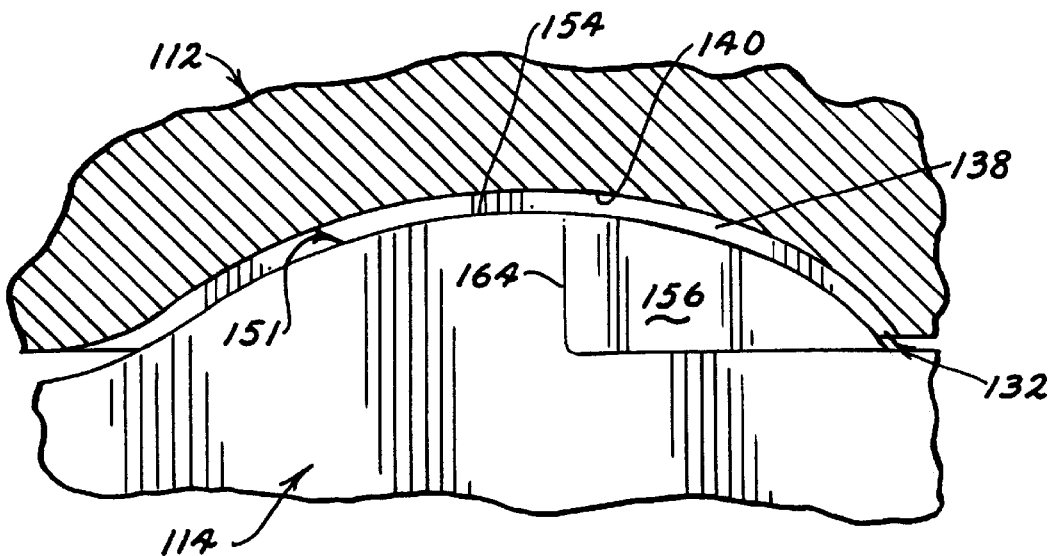
FIG. 20 is a partially broken away cross-sectional view of the recess similar to that shown in FIG. 19 but generally showing a lateral side portion of a leaflet within the recess when the leaflet is in a fully closed position as shown diagrammatically in FIG. 17.

When the leaflet 114 is in the fully closed position, the initial movement of the leaflet is more likely to be followed immediately by a pivotal movement, because the cylindrical diamond-shaped surface 154 and the cylindrical recess bottom surface 140 are more closely mated as shown in FIG. 20 and the separation allowing translational movement from end to end is more limited. The leaflet 114 is likely to slip quickly from the upper side edge 134 toward the lower side sidewall 138 of the leaflet 114. The leaflet will only begin to pivot after the bottom side fulcrum edge 164 is engaged with the lower side sidewall 138. It will be appreciated, however, that the mechanism employed by the respective leaflets for pivoting is still a matter of inquiry and is not fully understood at this time. It is believed, however, this dynamic pivot mechanism allows for faster opening and closing of the respective valves 110. When the valve is in the open position, and the flow direction changes from antegrade to retrograde, it is believed that the leaflet 114 begins its linear motion immediately with the change in the flow direction and the linear momentum is transferred into angular momentum as soon as the top side fulcrum edge or pivot 166 contacts the seat 136 proximate the upper edge 134 of the recess 132. This is believed to result in quicker closing than is exhibited by prior art devices.

It is believed that the preferred bileaflet heart valve prosthesis 110 of the present invention provides for a lowered thrombus potential due to the consideration given to access for washing in both the antegrade and retrograde directions. Furthermore, the dynamic pivot mechanism of the preferred leaflets 114 in cooperation with the preferred recesses 132 are believed to provide for faster opening and closing of the valve and less friction in the pivot area due to the use of a "rolling" pivot mechanism wherein the pivot activity changes focus from the top side fulcrum edge 166 to the bottom side fulcrum edge 164. The preferred valve 110 also provides for a minimized travel angle "k'" between the fully opened position and the fully closed position. It is believed that the travel angle provided in the preferred valve 110 may represent at least about 15–10° reduction in the travel angle as compared to many of the prior art devices. This reduction in the travel angle is believed to minimize angular velocity, wear, cavitation potential, and regurgitation volume, while increasing overall efficiency.

The upper edges 134 for the preferred leaflets 114 are believed to slow the leaflet 114 just before closure due to the presence of significant amounts of fluids which may be "squeezed" or compressed against the sidewall 126 of the annular base 112. Because the seats slow the leaflet 114 just before closure, they are believed to have a minimizing effect on the cavitation potential. It is also believed that the use of discontinuous seats, or seats which diminish prior to continuing into a seat extending from an opposite recess allows for a slight increase in regurgitation potential proximate the center portion of the leaflet where cavitation potential is generally highest due to the likelihood that this area is likely to be subjected to a greater angular velocity as it comes toward closure against the sidewall 126. The seats 134 also decrease leakage or regurgitation proximate the lateral sides 129 of the annular base 112 when the leaflets 114 are in the closed position. The seats 134 are also believed to provide for increased antegrade flow to wash the flow channels or recesses 132 as the leaflets 114 close. As the leaflets 114 close the fluid in the recesses 132 begins to be "squeezed" or compressed within an upper portion of the recess distal to the transverse sides 131 of the annular base 112. The width of the seats 134 decreases as they extend from the recess 132 to the transverse side 131. Since there is no seat 134 in the center most region of the transverse side 131 in the preferred bileaflet heart valve 110, the fluid "squeezed" or compressed against the seats 134 is generally believed to be released through the bore 116 after it washes at least a portion of the seat 134. While the leaflets 114 are in the closed position, the seats 134 serve to reduce retrograde leakage or regurgitation and at least a portion of the retrograde flow is channeled around the diamond surface 154, so as to thoroughly wash these areas when the leaflets 114 are in a closed position.

Figure 21:
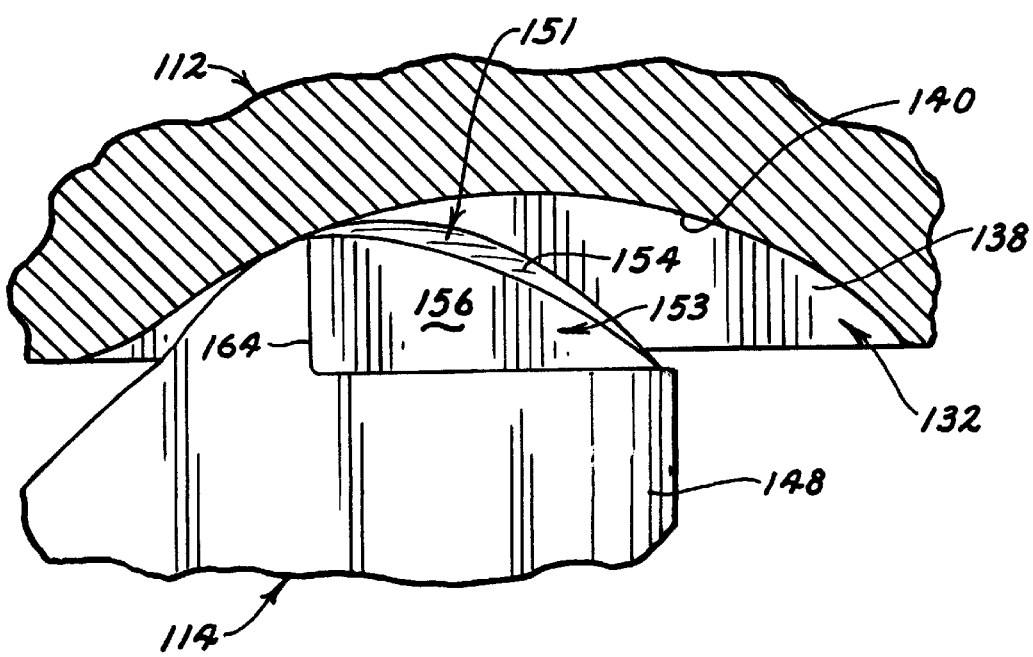
FIG. 21 is a partially broken away cross-sectional view similar to FIG. 20, but showing the leaflet in an open position as shown in FIG. 1.

The bottom surface of the recess 132 is in the form of a curvilinear cylindrical surface and is considered to have a generally cylindrical shape. As used herein, cylindrical surface or cylindrical shape means a surface formed by linear translation of a curve, or a surface which has a radius similar to a portion of a surface of a cylinder. The diamond surface 154 at the lateral sides 151 of the leaflets 114 have a cylindrical shape which is "consistent" with or "mates" with the cylindrical recess bottom surfaces 140 of the recesses 132. However, as shown in FIG. 20, the diamond surface 154 is consistent with and mates with the bottom surface 140 of the recess 132 only when the leaflet 114 is in the closed position. However, when the leaflet is in the open position, as shown in FIG. 21, and as previously discussed, significant room for translational movement is provided. Furthermore, it will be appreciated that the bottom surface of the recess 140 and the matched cylindrical diamond surface 154 of the leaflet 114 will not be in alignment when the leaflet is in any position other than a fully closed position, thus allowing for significant clearance between the extreme edges of the diamond surfaces 154 and the extreme edges of the recesses 132. Because of the increased potential for translational movement when the leaflets 114 are in positions other than the fully closed position, the leaflets 114 will exhibit greater translational freedom for motion than is possible with prior art valves having parallel or matched surfaces in all positions as described and defined in descriptions of the prior art devices.

Figure 16:
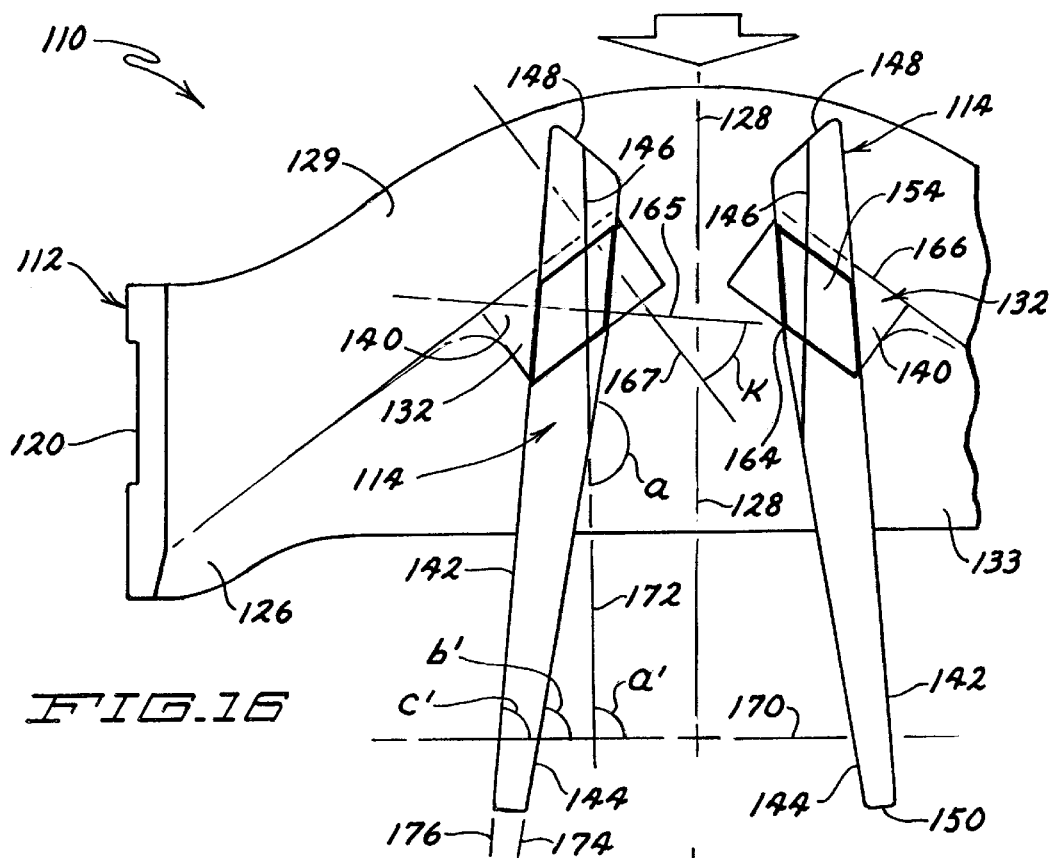
FIG. 16 is a diagrammatic cross-sectional view of the preferred bileaflet heart valve shown in FIG. 1 with the leaflets in a fully open position.

As shown particularly in FIG. 16, the flat planar surface 146 of the central bevel 145 and the peripheral bevel 144 of the bottom surface of the leaflet each lie generally in a plane respectively designated by tangent lines 172 and 174. As measured by the angle "a" between tangent lines 172 and 174, the peripheral bevel 144 and the flat planar surface 146 of the central bevel 145 lie generally in planes which lie at an angle to one another. In preferred embodiments this angle will be less than 180°, or preferably at an angle of about 161° to about 178°, more preferably about 166° to about 173°. In preferred embodiments, the angle "a" will be about 167° to about 172°. In the most preferred embodiment under consideration, the angle "a" is about 169°. This bevel in the bottom surfaces of the leaflet 114, allows the angle of incidence for a flow of blood in the retrograde direction parallel with the longitudinal axis 128 to be a greater angle of incidence in respect to the peripheral bevel 144 than with the flat planar surface 146 of the central bevel 145. This is believed to be advantageous for at least two reasons. First, since there is a greater angle of incidence, the force of the blood flowing in the retrograde direction will have greater impact upon the leaflet 114 and cause it to pivot toward the fully closed position more rapidly than might otherwise be expected. Furthermore, the difference between the respective bevels, and the angle of the tangent line 176 to the top planar surface 142 allow the peripheral edge 150 to have a shorter radial closing distance to travel before the leaflet 114 is in the fully closed position than might be expected for a leaflet having parallel surfaces.

In preferred embodiments, the angle of the plane in which the flat planar surface 146 of the central bevel 145 rests, to a horizontal plane 170, which angle is consistent with the angle between tangent line 172 and the plane 170, will be an angle "a'". In preferred embodiments, "a'" may range from about 84° to about 97°, preferably about 86° to about 95°, more preferably about 88° to about 94°, more preferably about 90° to about 92°, more preferably more than 90°, and in the most preferred embodiments, "a'" will be either 91°, or 91° or more. Similarly, the angle between the plane in which the peripheral bevel 144 rests, and the horizontal plane 170 may be measured by taking the angle "b'" between the tangent line 174 and the horizontal plane 170. In preferred embodiments, the angle "b'" will be less than 87°, preferably less than 86°. In preferred embodiments, "b'" will range from about 78° to about 84°, preferably about 80° to about 82°, and most preferably, it will be about 81°. Similarly, the angle of the plane in which the top planar surface 142 of the top side of the leaflet 114 rests, will lie at an angle "c'" to the horizontal plane 170 as measured between the tangent line 176 and the horizontal plane 170 when the leaflet is in the fully open position. In preferred embodiments, "c'" is greater than about 78° and less than 90°, and preferably in a range of from about 82° to about 89°, preferably about 84° to about 88°. In the most preferred embodiment, "c'" is about 86°.

As shown particularly in phantom in FIG. 17, when the leaflet 114 begins to pivot from the fully open position to the fully closed position in response to force exerted upon the peripheral bevel 144, the force is believed to result in an initial translational movement of the leaflet to lift leaflet 114 within the recess 132. When the leaflet 114 has reached the fully closed position shown diagrammatically in FIG. 17, an area on the top planar surface 142 proximate the peripheral edge 150 generally proximate the respective lateral sides 151 will abut against the seat 136 on either lateral side 129 and extending at least partially into the adjacent transverse side 131. When the leaflet 114 is in the fully closed position, the respective mating edges 148 will generally rest against one another while generally allowing at least some retrograde regurgitation of blood between the respective mating surfaces 148.

It will be appreciated that the preferred embodiment of the bileaflet heart valve prosthesis 110 of the present invention will not have any sharp edges and that all edges will in fact be polished, smoothed or feathered so as to minimize shearing of blood as it passes over any of these edges. These smooth "transitions" between surfaces of all kinds will be obtained by shaving and polishing all edges so that the edges are rounded and have a smooth transition from one plane to another. Any radial surfaces of course will be polished as well.

Figure 24:
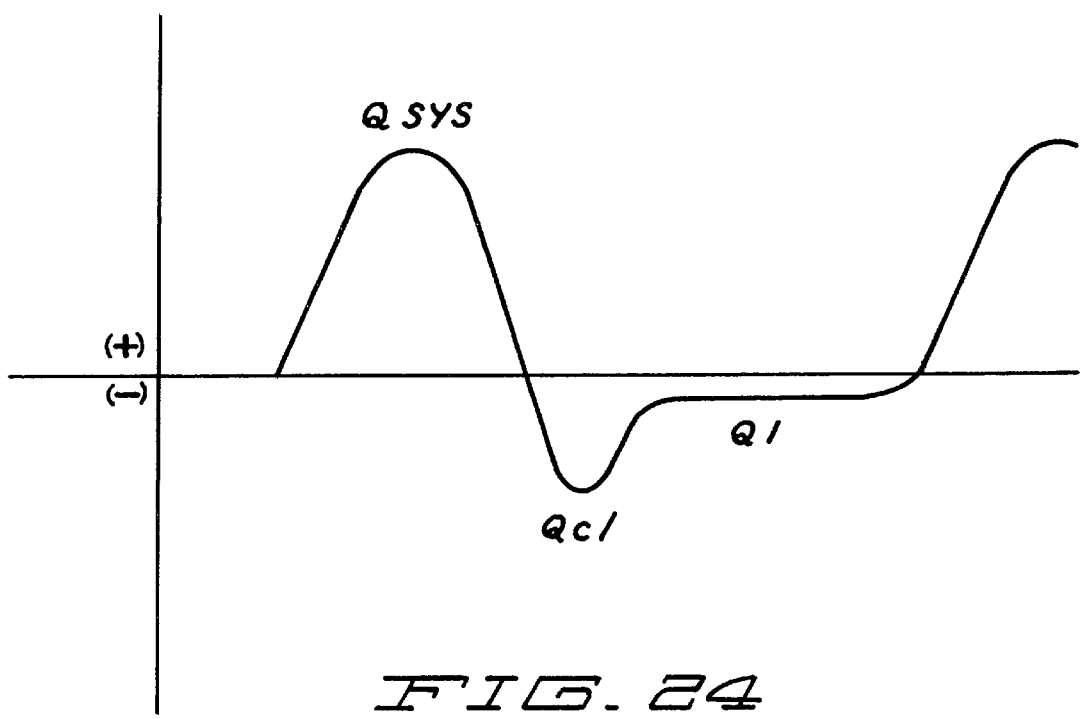
FIG. 24 provides a graphic representation of the quantity of blood flowing through a bileaflet heart valve during a single heart contraction cycle wherein the positive quantity indicates blood flowing in an antegrade direction and the negative quantity below the "y" axis indicates the quantity of blood flowing in the retrograde direction.
Figure 25:
FIG. 25 is a perspective view of a monoleaflet heart valve with anterior orientation as known to the prior art.

As shown in FIG. 22, the amount of regurgitation of blood in the retrograde direction is believed to be significant enough to provide appropriate cleansing of the valve 110. Heart valves are generally designed with at least some regurgitation in mind so long as the regurgitation does not reduce the efficiency of the heart. It is believed that the regurgitation is important to permit the washing of the various surfaces of the present prosthetic device. FIG. 24 generally provides a representation of the quantity (Q) of blood flowing through a bileaflet heart valve during a contraction cycle when the valve is in the aortic position. During systole, the quantity of blood passing through the valve in the antegrade direction (+) is fairly significant. As the force from the contraction diminishes from its highest point, indicated at the apex of the curve (Qsys), until the antegrade flow ends and blood begins to flow in the retrograde direction (−), the leaflets 114 remain in an open position. The retrograde flow then begins to push the leaflets 114 toward the closed position at the lowest point of the curve below the "y" axis (Qcl). As the leaflets 114 close, most of the retrograde flow is obstructed, but not all of it. The remaining retrograde flow is due to leakage around the leaflets 114. The retrograde leakage (Ql) has been discussed herein and is believed to have a positive effect in respect to washing the various surfaces of the prosthetic heart valve, in that this "regurgitation" will "wash" the surfaces to reduce stagnation of blood as a measure against potential thrombus.

Figure 6:
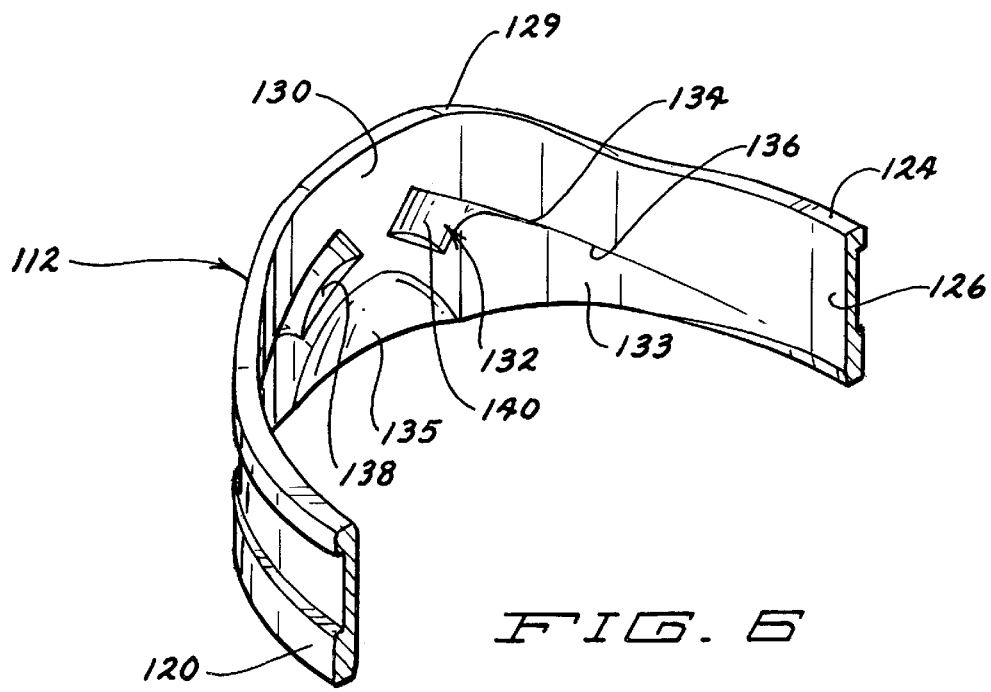
FIG. 6 is a partially broken away elevated perspective view of the annular base of the preferred bileaflet heart valve shown in FIG. 1.
Figure 7:
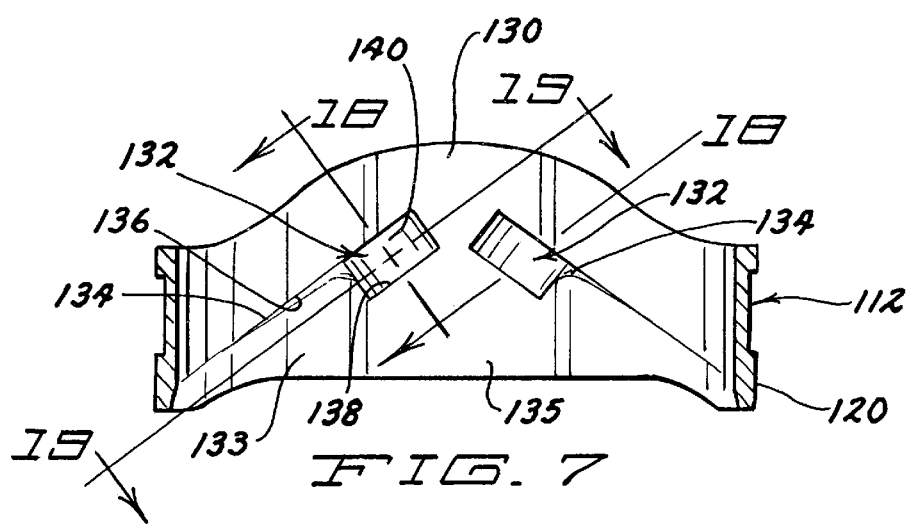
FIG. 7 is a cross-sectional side view of the lateral side of the annular base of the preferred bileaflet heart valve shown in FIG. 1.
Figure 8:
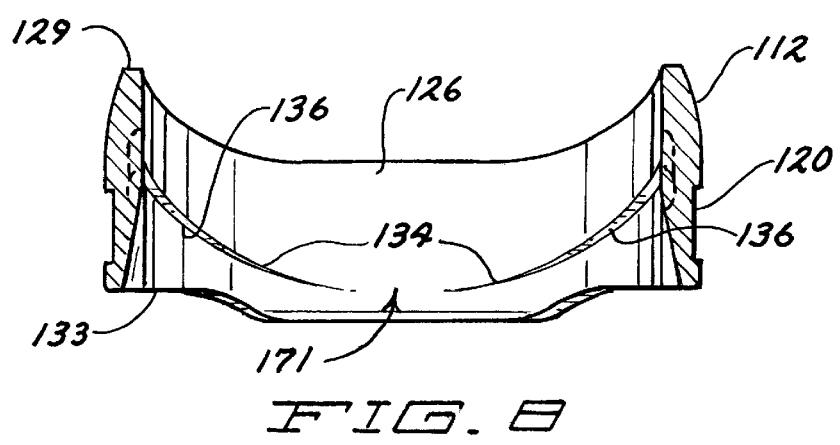
FIG. 8 is a cross-sectional side view of the traverse side of the annular base of the preferred bileaflet heart valve shown in FIG. 1.
Figure 9A:
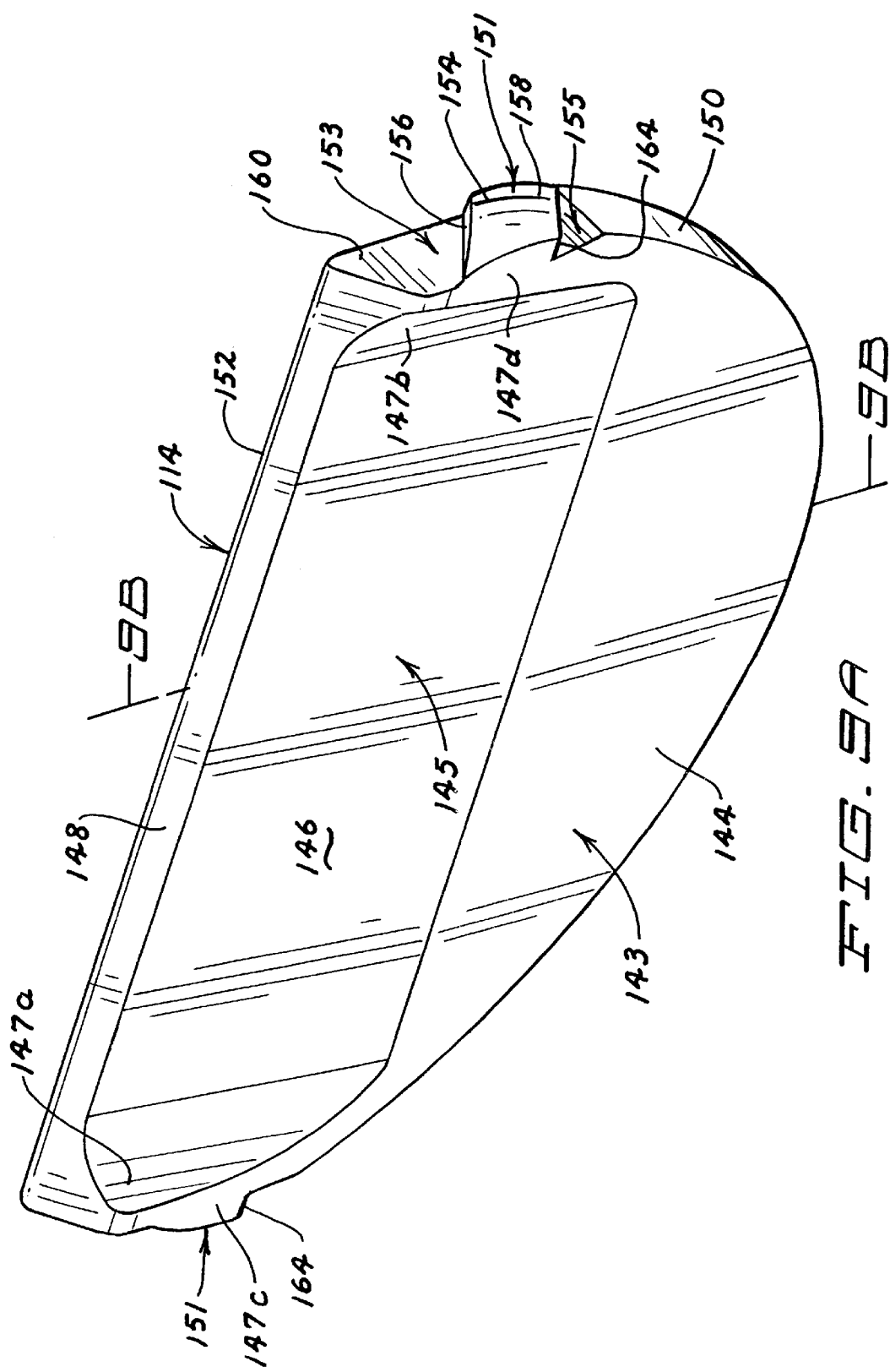
FIG. 9A is an elevated perspective view of the bottom side of the preferred leaflet shown in FIG. 1.
Figure 10:
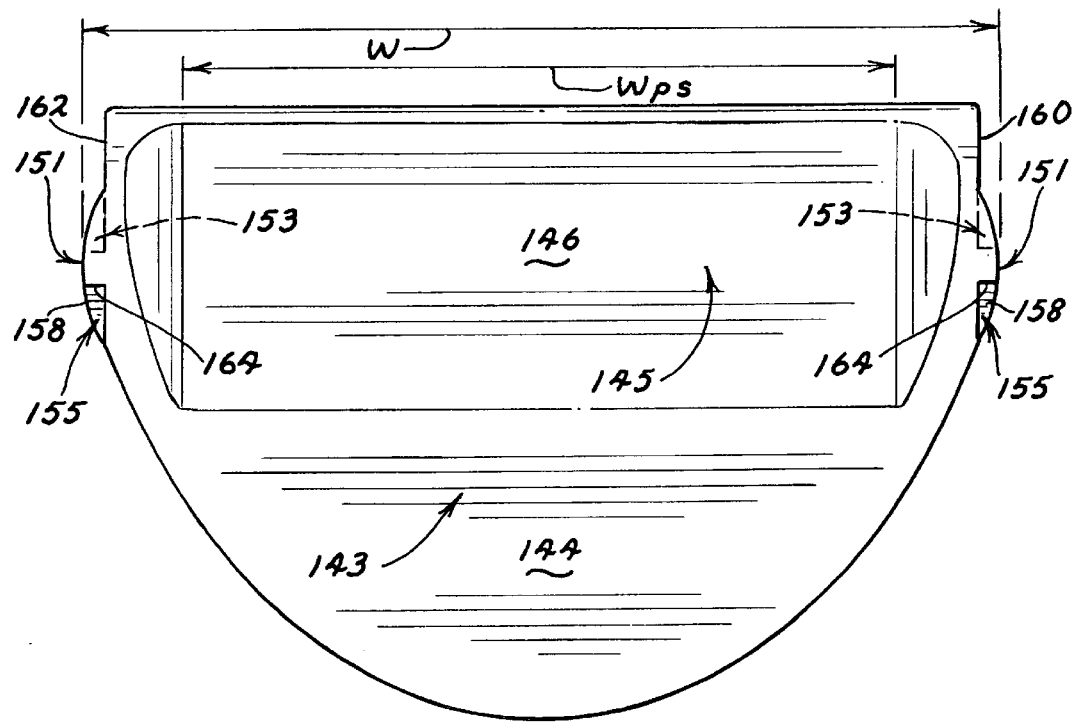
FIG. 10 is a bottom plan view of a leaflet of the preferred bileaflet heart valve shown in FIG. 1.
Figure 11:
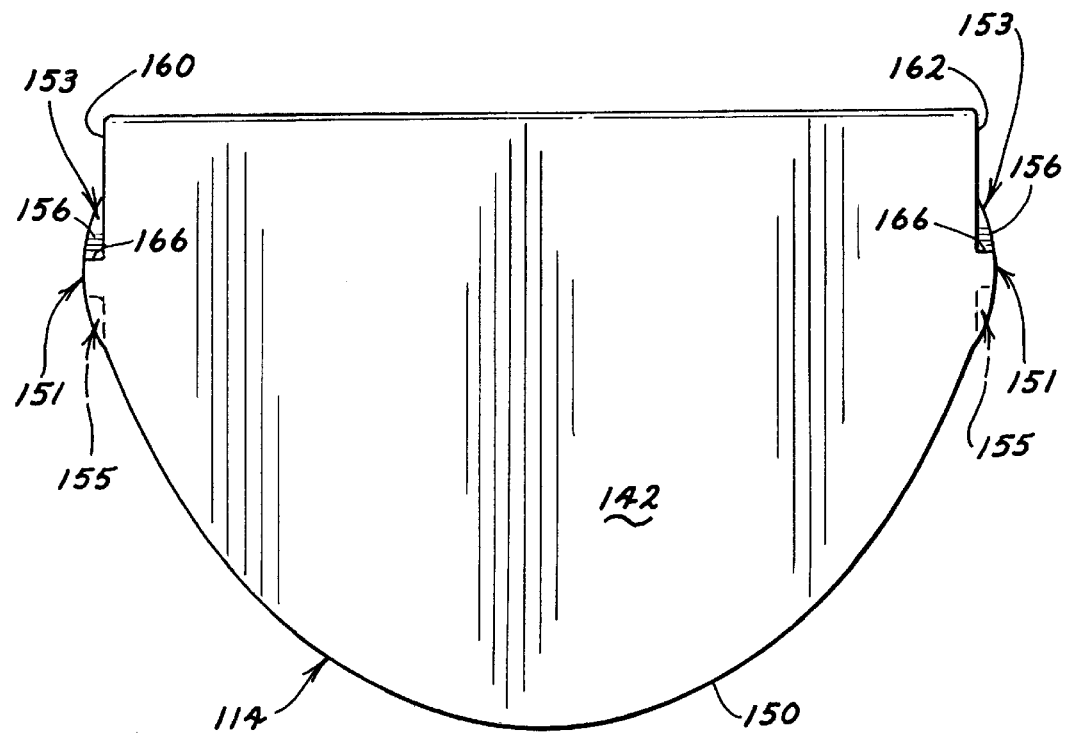
FIG. 11 is a top plan view of a leaflet of the preferred bileaflet heart valve shown in FIG. 1.
Figure 23:
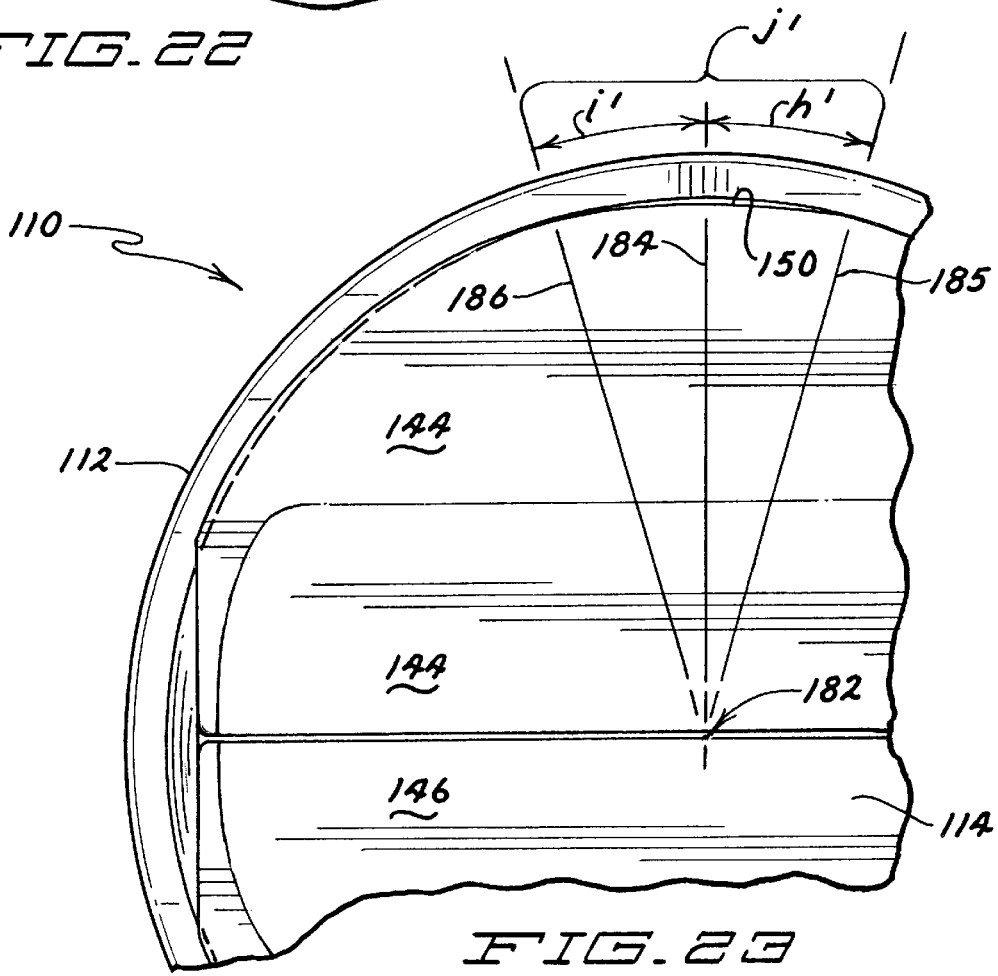
FIG. 23 is a partially broken away bottom plan view of the preferred bileaflet heart valve shown in FIG. 22 when the leaflets are in a fully closed position.

As shown particularly in FIGS. 6 and 7 and demonstrated diagrammatically in FIG. 23, the upper edge 134 blends or "feathers" into the inner wall 126 of the annular base 112, as does the seat 136, in preferred embodiments. It is believed that this has a very positive effect upon preservation of the integrity of the top planar surface 142 of the respective leaflets 114 by reducing cavitation potential. This is particularly true in an area approximately 15° to either side of a center line 184 bisecting a leaflet 114, and in the areas most proximate to the peripheral edge 150. The potential for negative effects of cavitation upon the top planar surface 142 is also reduced by the shortened travel angle "k'" between the location of the top planar surface 142 when the leaflet is in the fully open position, and the top planar surface 142 when the leaflet is in the fully closed position as represented by tangent line 179 of FIG. 17. Because the preferred leaflet 114 of the present invention has a "double-beveled" bottom surface, the position of the top planar surface 142 in relation to the side wall 126 can be minimized to reduce the radial distance "k'" traveled by the top planar surface 142 in moving to the closed position. In this way, the angular speed of the movement of the most distal portion of the top planar surface 142 proximate the peripheral edge 150, where the cavitation potential is generally believed to be the greatest, is diminished gradually when the leaflet 114 approaches the closed position. Cavitation potential is also minimized because the distance is minimized by the beveled design of the leaflets 114. In this regard, it will be appreciated that the leaflet will continue to gain speed as it pivots through a greater radial distance. Therefore, by minimizing the radial distance between the open position and the closed position, the radial speed of the leaflet 114 can be minimized. In preferred embodiments, the travel angle "k'" will be from about 37° to about 58°, preferably about 39° to about 56°, even more preferably about 40° to about 55°, and most preferably about 45° to about 50°. Cavitation potential is also reduced because the seats 136, extending from the respective recesses 132 on the respective lateral sides of the leaflet 114, help to slow the closure or "cushion" the closure of the leaflet against the side wall 126 because the blood between the peripheral edge 150 and the proximate portions of the top planar surface 142 must be "squeezed" out of the intervening space adjacent the respective seat 136 as the leaflet 114 is pivoting toward the fully closed position. Furthermore, a gap 171 (shown in FIG. 8) between the seats 136 of the opposing lateral sides extending into the transverse side permits a continuing flow of blood in the retrograde direction which also helps to prevent the formation of a vacuum on the top planar surface 142 proximate the peripheral edge 150 which is generally the genesis of cavitation damage on the planar surfaces of a leaflet 114. The "cushioning" effect of the partial or "discontinuous" seats 136 also helps to prevent stress to other portions of the leaflet 114 as they collide with the side wall 126 or the seat 136.

In FIG. 23, a center line 184 extending from a center point 182 is shown superimposed upon a bottom surface of a leaflet 114. In preferred embodiments, the respective seats 136 extending from respective recesses 132 will extend only as far as the radius lines 185 and 186 which are radially equidistance from the center line 184. For this reason, the radial angle "i'" will equal the radial angle "h'" between the radius lines 186, 185 and the center line 184, respectively, and the radial angle "j'" will equal twice either of the equal angles "i'" and "h'". In preferred embodiments, the radial angle of "j'" will range from about 5° to about 55°, preferably about 10° to about 50°, more preferably about 15° to about 45°, even more preferably about 20° to about 40°, even more preferably about 25° to about 35°, and even more preferably about 30°. The reason for limiting the extension of the seats 136 entirely through the inner wall 126 proximate the transverse surface 131 is in part because of a desire to minimize the cavitation potential which is generally greatest within 15° on either side of a center line 184 bisecting the top planar surface 142 of a pivotal leaflet 114 of a bileaflet heart valve. It will be understood that the area having the greatest cavitation potential is likely to be at the most distal portion of the top planar surface 142 from the center point 182, because it is this portion of the leaflet 114 which gains the most angular speed when the leaflet is pivoting toward closure and is most capable of generating the force required to create cavitation bubbles on the top planar surface 142. Therefore, eliminating the seat 136 in this particular area, is expected to minimize cavitation potential by permitting more regurgitation through the gap 171.

While the preferred embodiments of the above bileaflet heart valve 10, 110 have been described in detail with reference to the attached drawings, it will be understood that various changes and adaptations may be made in the bileaflet heart valve 10, 110 without departing from the spirit and scope of the appended claims. It is to be understood that even though numerous characteristics and advantages of various embodiments of the present invention have been set forth in the foregoing description, together with details of the structure and function of various embodiments of the invention, this disclosure is illustrative only and changes may be made in detail, especially in matters of shape, size and arrangement of parts, within the principles of the present invention, to the full extent indicated by the broad general meaning of the terms in which the appended claims are expressed.

What is claimed is:

1. A bileaflet heart valve prosthesis for controlling a circulation of a fluid within a heart of a patient, said bileaflet heart valve prosthesis comprising: an annular base and first and second leaflets, the first leaflet and the second leaflet being mounted within the annular base for pivotal movement between a fully closed position and a fully open position, the annular base defining a vertical bore extending through the base; each of the respective leaflets having first and second sides, the first side being a top side and the second side being a bottom side, the bottom sides of the respective leaflets generally facing one another when the respective leaflets are in an open position; each bottom side having an upper half and a lower half, a major portion of the upper half providing an upper surface lying generally in a first plane and a lower half providing a lower surface lying generally in a second plane, the first plane lying at an angle to the second plane; a third plane passing through a horizontal cross-section of the annular base, the first and second planes lying at angles to the third plane when the leaflets are in either the open or closed positions; wherein the first plane of each of the respective leaflets extends beyond an angle of 90 with respect to the third plane when the leaflets go from the fully closed position to the fully open position, the annular base having a first lateral side having a first lateral surface, a second lateral side having a second lateral surface, and a pair of transverse sides individually disposed between the first and second lateral sides, the annular base defining a first recess extending radially outward into the annular base from and communicating with the bore, and a second recess extending radially outward into the annular base from and communicating with the bore, the first recess being disposed within the first lateral side, the second recess being disposed within the second lateral side, wherein at least a first side portion of the first leaflet is received within the first recess and at least a second side portion of the first leaflet is received within said second recess to retain the first leaflet within the annular base, wherein the annular base further defines third and fourth recesses extending radially outward into the annular base from and communicating with the bore, the third recess being disposed within the first lateral side and the fourth recess being disposed within the second lateral side, wherein at least a third side portion of the second leaflet is received within the third recess and at least a fourth side portion of the second leaflet is received with the fourth recess to retain the second leaflet within the annular base; the first, second, third and fourth side portions of the respective leaflets each having a plurality of recess engagement surfaces, two of the plurality of recess engagement surfaces meeting to form a first fulcrum edge and two of the plurality of recess engagement surfaces meeting to form a second fulcrum edge removed from the first fulcrum edge, each of the recesses having an upper and lower recess side surface, wherein each of the respective first and second fulcrum edges engage an upper or lower recess side surface of the recess in which the respective side portion is engaged when the respective leaflet pivots either from the fully open position to the fully closed position or from the fully closed position to the fully open position such that engagement between one of the respective fulcrum edges and the respective side surface of each of the respective side recesses is changeable from engagement with a side surface by the first fulcrum edge to engagement with a side surface by the second fulcrum edge as the respective leaflet pivots from one position to the other.

2. The bileaflet heart valve prosthesis of claim 1, wherein the first and second planes lie at first and second angles respectively to the third plane passing through the horizontal cross-section of the annular base when the respective leaflets are in the fully open position, the first angle being greater than 90° and the second angle less than 87°.

3. The bileaflet heart valve prosthesis of claim 2, wherein the angle between the first plane and the second plane is from about 161° to about 178°.

4. The bileaflet heart valve prosthesis of claim 1, wherein the respective top sides have top surfaces which lie generally in respective top planes and each of the top planes changes position from a first position to a second position when the respective leaflet changes position from the fully open position to the fully closed position, wherein a travel angle is an angle between the respective top plane when the leaflet is in the first position and the respective top plane when the leaflet is in the second position, and wherein the travel angle for each of the first and second leaflets is from about 40° to about 55°.

5. The bileaflet heart valve prosthesis of claim 4, wherein a horizontal plane, which is perpendicular to the lateral sides of the annular base, passes through a horizontal cross-section of the base, and each of the respective top planes lie at a greater angle to the horizontal plane than the second plane on the respective lower surface.

6. The bileaflet heart valve prosthesis of claim 1, wherein each of the respective leaflets having first and second sides, the first side being a top side and the second side being a bottom side, the bottom sides of the respective leaflets generally facing one another when the respective leaflets are in an open position; each bottom side having an upper surface lying generally in a first plane and a lower surface lying generally in a second plane, the first plane lying at an angle to the second plane.

7. A bileaflet heart valve prosthesis for controlling a circulation of a fluid within a heart of a patient, said bileaflet heart valve prosthesis comprising: an annular base and first and second leaflets, the first leaflet and the second leaflet being mounted within the annular base for pivotal movement between a fully closed position and a fully open position, the annular base defining a vertical bore extending through the base; each of the respective leaflets having first and second sides, the first side being a top side and the second side being a bottom side, the bottom sides of the respective leaflets generally facing one another when the respective leaflets are in an open position; each bottom side having an upper half and a lower half, a major portion of the upper half providing an upper surface lying generally in a first plane and a lower half providing a lower surface lying generally in a second plane, the first plane lying at an angle to the second plane; a third plane passing through a horizontal cross-section of the annular base, the first and second planes lying at angles to the third plane when the leaflets are in either the open or closed positions; wherein the first plane of each of the respective leaflets extends beyond an angle of 90 with respect to the third plane when the leaflets go from the fully closed position to the fully open position, the annular base defining a bore extending through the base, the base having a longitudinal axis oriented generally in parallel with the bore and the circulation of the fluid through the bore, the annular base having a first lateral side having a first lateral surface, a second lateral side having a second lateral surface, and a pair of transverse sides individually disposed between the first and second lateral sides, the annular base defining a first recess extending radially outward into the annular base from and communicating with the bore, and a second recess extending radially outward into the annular base from and communicating with the bore, the first recess being disposed within the first lateral side, the second recess being disposed within the second lateral side, the first recess having a first recess bottom surface, the first recess bottom surface intersecting the first lateral surface of the base such that the first recess bottom surface and the first lateral surface form a first junction, a first recess entrance angle being the largest of a plurality of angles between a first line generally tangential with the first lateral surface proximate the first junction and any of an infinite number of second lines intersecting the first line and generally tangential with any portion of the first recess bottom surface proximate the first junction, the second recess having a second recess bottom surface intersecting the second lateral surface such that the second recess bottom surface and the second lateral surface form a second junction, a second recess entrance angle being the largest of a plurality of angles between a third line tangential with the second lateral surface proximate the second junction and any of an infinite number of fourth lines intersecting the third line and tangential with any portion of the second recess bottom surface proximate the second junction; wherein at least a first side portion of the first leaflet is received within the first recess and at least a portion of the first leaflet is received within said second recess to retain the first leaflet within the annular base; the improvement characterized in that each of the first and second recess entrance angles are less than about 35.

8. The bileaflet heart valve prosthesis of claim 7 wherein the first and second recess entrance angles range from about 18° and about 34°.

9. The bileaflet heart valve prosthesis of claim 7 wherein the first and second recess bottom surfaces are cylindrical surfaces.

10. The bileaflet heart valve prosthesis of claim 7 wherein the annular base further define third and fourth recesses extending radially outward into the annular base from and communicating with the bore, the third recess being disposed within the first lateral side and the fourth recess being disposed within the second lateral side, the third recess having a third recess bottom surface intersecting the first lateral surface such that the third recess bottom surface and the first lateral surface form a third junction, a third recess entrance angle being the largest of a plurality of angles between a fifth line generally tangential with the first lateral surface proximate the third junction and any of an infinite number of sixth lines intersecting the fifth line and generally tangential with any portion of said third recess bottom surface proximate the third junction, the fourth recess having a fourth recess bottom surface intersecting the second lateral surface, the fourth recess bottom surface and the second lateral surface intersecting to form a fourth junction, a fourth recess entrance angle being the largest of a plurality of angles between a seventh line generally tangential with the second lateral surface proximate the fourth junction and any of an infinite number of eighth lines intersecting the seventh line and generally tangential with any portion of the fourth recess bottom surface proximate the fourth junction, each of the third and fourth recess entrance angles being less than about 35°, wherein at least a third side portion of the second leaflet is received within the third recess and at least a fourth side portion of the second leaflet is received with the fourth recess to retain the second leaflet within the annular base.

11. The bileaflet heart valve prosthesis of claim 9, the first bileaflet having a peripheral edge, wherein the respective side portions of the first leaflet which are received within the first and second recesses each have a cylindrical surface along the peripheral edge proximate the respective side portions received within the respective recesses.

12. The bileaflet heart valve prosthesis of claim 11, the first leaflet having a complimentary pair of notches in the peripheral edge proximate each of the respective side portions of the first leaflet which are received within the respective first and second recesses, wherein the complimentary pair of notches cooperate to permit the leaflet to pivot within the respective recess.

13. The bileaflet heart valve prosthesis of claim 9, wherein each of the respective side portions of the respective leaflets have a cylindrical side surface along a peripheral edge of the leaflet proximate the respective side portion which is received within the respective recess, wherein the respective cylindrical side surfaces mate with the respective cylindrical bottom surfaces of the respective recess in which the respective side portions are received when the respective leaflets are in the closed position.

14. The bileaflet heart valve prosthesis of claim 9, the first bileaflet having a peripheral edge, wherein the respective side portions of the first leaflet, which are received within the first and second recesses, each have a cylindrical surface along the peripheral edge proximate the respective side portions received within the respective recesses.

15. The bileaflet heart valve prosthesis of claim 14, the first leaflet having a complimentary pair of notches in the peripheral edge proximate each of the respective side portions of the first leaflet which are received within the respective first and second recesses, wherein the complimentary pair of notches cooperate to permit the leaflet to pivot within the respective recess and the cylindrical surfaces of the respective peripheral edges mate with the cylindrical bottom surfaces of the respective recesses in which the respective recesses in which the respective side portions are received when the first leaflet is in the closed position.

16. A bileaflet heart valve prosthesis for controlling a circulation of a fluid within a heart of a patient, said bileaflet heart valve prosthesis comprising: an annular base and first and second leaflets, the first leaflet and the second leaflet being mounted within the annular base for pivotal movement between a fully closed position and a fully open position, the annular base defining a vertical bore extending through the base; each of the respective leaflets having first and second sides, the first side being a top side and the second side being a bottom side, the bottom sides of the respective leaflets generally facing one another when the respective leaflets are in an open position; each bottom side having an upper half and a lower half, a major portion of the upper half providing an upper surface lying generally in a first plane and a lower half providing a lower surface lying generally in a second plane, the first plane lying at an angle to the second plane; a third plane passing through a horizontal cross-section of the annular base, the first and second planes lying at angles to the third plane when the leaflets are in either the open or closed positions; wherein the first plane of each of the respective leaflets extends beyond an angle of 90 with respect to the third plane when the leaflets go from the fully closed position to the fully open position, the annular base having a first lateral side having a first lateral surface, a second lateral side having a second lateral surface, and a pair of transverse sides individually disposed between the first and second lateral sides, the annular base defining a first recess extending radially outward into the annular base from and communicating with the bore, and a second recess extending radially outward into the annular base from and communicating with the bore, the first recess being disposed within the first lateral side, the second recess being disposed within the second lateral side, wherein at least a portion of the first leaflet is received within the first recess and at least a portion of the first leaflet is received within said second recess to retain the first leaflet within the annular base, wherein the annular base further defines third and fourth recesses extending radially outward into the annular base from and communicating with the bore, the third recess being disposed within the first lateral side and the fourth recess being disposed within the second lateral side, wherein at least a portion of the second leaflet is received within the third recess and at least a portion of the second leaflet is received with the fourth recess to retain the second leaflet within the annular base; wherein each leaflet has an upper surface and a curved peripheral edge and each recess has an upper side and a lower side, the upper side extending from the respective recess proximate the respective lateral side to a location on an adjacent transverse side, the upper edge of each recess forming a seat against which an area on the upper surface, proximate the curved peripheral edge, of a leaflet engaged within the respective recess, can abut when the leaflet is in the closed position, the improvement characterized in that each of the respective upper edges forms a seat which extends from one recess toward another and diminishes to become a smooth surface which is flush with the respective lateral surface.

17. The bileaflet heart valve prosthesis of claim 13, wherein each upper side has an end point where the seat diminishes into the respective lateral surface and no longer provides a seat against which the upper surface proximate the peripheral edge can abut, wherein the annular base has an inner wall which includes the lateral surface and the annular base has a radial distance which extends 360° around the inner wall, wherein the upper side extending from the first recess is the first upper side and the upper side extending from the second recess is the second upper side and the radial distance between the respective end points of the first and second upper sides is from about 5° to about 55°.

* * * * *